United States Patent [19]

Rasmussen

[11] Patent Number: 5,679,540
[45] Date of Patent: Oct. 21, 1997

[54] CLONING AND IDENTIFICATION OF A TWO COMPONENT SIGNAL TRANSDUCING REGULATORY SYSTEM FROM *BACTEROIDES FRAGILIS*

[75] Inventor: Beth Ann Rasmussen, Nyack, N.Y.

[73] Assignee: American Cyanamid Company, Wayne, N.J.

[21] Appl. No.: 23,764

[22] Filed: Feb. 26, 1993

[51] Int. Cl.$^6$ ............................ C12P 21/02; C07H 21/04; C12N 1/21; C12N 15/70
[52] U.S. Cl. .................. 435/69.1; 435/194; 435/252.33; 435/380.1; 536/23.2; 536/23.7
[58] Field of Search ........................... 435/69.1, 194, 435/252.33, 320.1; 536/23.2, 23.7

[56] References Cited

U.S. PATENT DOCUMENTS 4,970,147  11/1990  Huala et al. ............................ 435/69.1

OTHER PUBLICATIONS

Dutta et al. (1996) *J. Biol. Chem.* 271(3):1424–1429.
Rasmussen et al. (1993) *Mol. Microbiol.* 7(5):765–776.
Stock, J.B., et al., *Nature*, 344, 395–400 (1990).
Comeau, D.E., et al., *J. Mol. Biol.*, 190, 37–44 (1986).
Makino, K., et al., *J. Mol. Biol.*, 192, 549–556 (1986).
Stock, A., et al., *Pro. Natl. Acad. Sci. USA*, 85, 1403–1407 (1988).
Jin, S., et al., *J. Bacteriol.*, 172, 4945–4950 (1990).
Weiss, V. and Magasanik, B.., *Proc. Natl. Acad. Sci. USA*, 85, 8919–8923 (1988).
Weber, R. F., and Silverman, P.M., *J. Mol. Biol.*, 203, 467–478 (1988).
Leroux, B., et al., *EMBO J.*, 6, 849–856 (1987).
Nixon, B.T., et al., *Proc. Natl. Acad. Sci. USA*, 83, 7850–7854 (1986).
Melchers, L.S., et al., *Nucleic Acids Research*, 14, 9933–9942 (1986).
Trach, K., et al., *J. Bacteriol.*, 170, 4194–4208 (1988).
Stock A., et al., *Proc. Natl. Acad. Sci. USA*, 82, 7989–7993 (1985).
Rasmussen, B.A., Gluzman, Y. and Tally, F. P., *Antimicrob.Agents. Chemother.*, 34 1590–1592 (1990).
Rasmussen, B. A., Gluzman, Y. and Tally, F. P., *Molecular Microbiol.*, 5, 1211–1219 (1991).
Miller, J. H., Experiments in molecular genetics, p. 433, Cold Spring Harbor Laboratory Press, Cold Spring Harbor, New York.
Sanger, F., et al., *Proc. Natl. Acad. Sci. USA*, 74, 5463–5467 (1977).
Vieira, J., and Messing, J., *Methods Enzymol.*, 153, 3–34 (1987).
Gold. L., and Stromo, G., "Translation initiation," pp. 1302–1307 in Neidhardt, F. et al., eds., *Escherichia coli* and *Salmonella typhimurium*, American Society for Microbiology, Washington, D.C. (1987).
Weisberg, G. W., et al., *J. Bacteriol.*, 164, 230–236 (1985).
Yager, T. D. and vonHippel, P.H., "Transcription and termination in *Escherichia coli*", pp. 1241–1275 in Neidhard, F. C., et al., eds., *Escherichia coli* and *Salmonella typhimurium*, American Society for Microbioloty, Washington, D.C. (1987).
Kyte, J., and Doolittle, R. F., *J. Mol. Biol*, 157 105–132 (1982).
Bankaitis, V.A., et al., *Cell*, 37, 243–252 (1984).
Hall, M.N. and Silhavy, T.J., *Mol. Biol.*, 146, 23–43 (1981).
Bachmann, B.J., "Derivations and genotypes of some mutant derivatives of *Escherichia coli* K–12", pp. 1190–1219 in Neidhardt, F.C., et al., eds., *Escherichia coli* and *Salmonella typhimurium*, American Society for Microbiology, Washington, D.C. (1987).
Salyers, A. A., et al., *Molecular Microbiol*, 4, 151–156 (1990).
Cohen, S.P., et al., *Antimicrob. Agents Chemother.*, 33, 1318–1325 (1989).
Pugsley, A.P., and Schnaitman, C. A., *J. Bacteriol.*, 133, 1181–1189 (1978).
Igo, M.M., et al., *Genes Dev.*, 3, 1725–1734 (1989).
Ninfa, A. J., et al., *Proc. Ntl. Acad. Sci. USA*, 85, 5492–5496 (1988).
Stock et al. (1989), Microbiological Reviews 53(4): 450–490.
Weaver et al. (1989), Genetics (Wm. C. Brown Publishers, Dubuque, Iowa), pp. 448–450.

*Primary Examiner*—Mindy Fleisher
*Assistant Examiner*—Nancy J. Degen
*Attorney, Agent, or Firm*—Darby & Darby

[57] ABSTRACT

This invention relates to a purified isolated DNA fragment of *Bacteroides fragilis* comprising a sequence for an operon containing two genes designated rprX and rprY. These genes encode two signal transducing regulatory proteins designated RprX and RprY. This invention further relates to the proteins RprX and RprY encoded by the operon. RprX and RprY affect the normal regulation of OmpF by OmpR and EnvZ.

20 Claims, 14 Drawing Sheets

FIG. 3A

```
                                                     -35
GGTTGTAGCTGCCGTTACATGCCATTGACAGTTCGTCGGTCGCCTCTTGA          405
              -10            -35
AACCTGCTTACTCATTAACAATGATTAAAGAAAGTAGATTTCTGAAGAGA          456
 -10   -10
AATCTTTAATTTTTATTAAATTGCAAACCAAAGGCATATACGTTTTGTT           507

ATAGTGGTCAGAATACGACCTAAAAAAACGTCTTTCGGTTAATTATAGAAA         558
                             S-D
CATCCCTGTTAAAACAGGTTAAGCTGTTAGGAGTGTTAATTAGGGAGTGTTA        609

ATTTTGTTGCTATGAAAAAGTCAACAATCTGGATATATTAGGCATTATTATGG       660
           M  K  K  S  T  I  W  I  L  G  I  I  M

GTCTTTCCTTTCTVAGTTGGCTCTCTATTTACAAGTGAGCTACATCGAAGAAA       711
 G  L  S  F  L  S  L  L  Y  L  Q  V  S  Y  I  E  E

TGGTGAGGATGCGTAAAGAGAACAATTTAATACATCCGTGCGAAATGCTTTGT       762
 M  V  K  M  R  K  E  Q  F  N  T  S  V  R  N  A  L

TTCAGGTTTCAAAGGATGTGGAGTATGATGAAACGCAACGTTGGCTGTTAG         813
 F  Q  V  S  K  D  V  E  Y  D  E  T  Q  R  W  L  L

AAGACATTACTGAAGCGGAACGTAGAACGCTGGCTCAGTCTTCTTCTACTA         864
 E  D  I  T  E  A  E  R  R  R  A  L  A  Q  S  S  S  T
```

FIG. 3B

```
CCGAACAGAAAAATGGTTTGATTCAGCAATCGGAGCGTTATAGGTTCAAGT   915
 T  E  Q  K  N  G  L  I  Q  Q  S  E  R  Y  R  F  K

CACCGGACGGAACCCTGTATTCGGAGTTTGAACTAAAGATGATTACCACCG   966
 S  P  D  G  T  L  Y  S  E  F  E  L  K  M  I  T  T

AGCCGTCGAAGGTGCCCAAAGCCATGATTTCGGAGAGACATGGCCGGAATA  1017
 E  P  S  K  V  P  K  A  M  I  S  E  R  H  G  R  N
                            HindIII CCATTCCGCAGACATCGCGAAGCTTGACCGACGCTATTAAAAATAGGTATA  1068
 T  I  P  Q  T  S  R  S  L  T  D  A  I  K  N  R  Y TGTATCAGCGTTTCCTGGTCTGACGATGTAGCTTTGCGGATGATTACAAAG  1119
 M  Y  Q  R  F  L  D  D  V  A  L  R  M  I  Y  K CAAGCGATAAGTCTAACTTTATTAATAATGGTATAGAGCTGCTATATCATTTTT 1170
 A  S  D  K  S  I  G  E  R  V  N  F  K  K  L  D  N ATCTGAAGTCTAACTTTATTAATAATGGTATAGAGCTGCTATATCATTTTT  1221
 Y  L  K  S  N  F  I  N  N  G  I  E  L  L  Y  H  F CGGTAATCGATAAAGATGGACGTGAGGTATATCGCTGTTCGGATTACGAAG  1272
 S  V  I  D  K  D  G  R  E  V  Y  R  C  S  D  Y  E AGGGAGGAAGTGAGGATTCTTATACCCAACCTCTGTTCCAAAATGATCCGC  1323
 E  G  G  S  E  D  S  Y  T  Q  P  L  F  Q  N  D  P
```

FIG. 3C

```
CTGCGAAGATGAGTATTGTGAAGGTGCACTTTCCGGGAAACAAAGATTATA   1374
 P  A  K  M  S  I  V  K  V  H  F  P  G  K  K  D  Y

TCTTCGACTCGGTTAGTTTTATGATCCCTTCGATGATATTCACTTTCGTAC   1425
 I  F  D  S  V  S  F  M  I  P  S  M  I  F  T  F  V

TGTTGATTACATTCATCTTCACTATTATCTACATCGTCTTCCGCAGAAGC    1476
 L  L  I  T  F  I  F  T  I  Y  I  V  F  R  Q  K  K

TGACAGAAATGAAGAATGACTTTATCAACAATATGACACGAGTTCAAGA     1527
 L  T  E  M  K  N  D  F  I  N  N  M  T  H  E  F  K
        EcoRV

CACCGATATCTACCATCTCGCTTGCCGCAGATGCTGAAAGATCCCGCAT     1578
 T  P  I  S  T  I  S  L  A  A  Q  M  L  K  D  P  A

TCGGGAAATCACCGGCAGATGTTCCAGGTGGAGAAAGTTCTTCAGATGTCTATG   1629
 V  G  K  S  P  Q  M  F  Q  H  I  S  G  V  I  N  D

AAACGAAGCGGTTGAGATTCGAGGTTGAGAAAGAACTGAAAGAACTGATGAGT    1680
 E  T  K  R  L  R  F  Q  V  E  K  V  L  Q  M  S  M

TCGACAGACAGAAAGCAACACTGAAGATGAAAGAACTCGATGCCAATGAGT   1731
 F  D  R  Q  K  A  T  L  K  M  K  E  L  D  A  N  E

TGATTTCCGGGGTTATCAATACGTTCGCTCTGAAGGTGGAACGCTATAATG   1782
 L  I  S  G  V  I  N  T  F  A  L  K  V  E  R  Y  N
```

FIG. 3D

```
GTAAGATTACATCGAACCTGAGGCTACCAATCCTGTTATATTTGCGGACG   1833
 G  K  I  T  S  N  L  E  A  T  N  P  V  I  F  A  D
AAATGCATATGACCAATGTGATATTCAACCTGATGGATAACGCGGTGAAAT  1884
 E  M  H  I  T  N  V  I  F  N  L  M  D  N  A  V  K
ACAAGAAGCCCGAAGAAGACCTGGTGCTCGACGTGAGAACCTGGAACGAAC  1935
 Y  K  K  P  E  E  D  L  V  L  D  V  Y  T  W  N  E
CCGGTAAACTGATGATTTCGATACAGGACAACGGTATTGGTATTAAAAAAG  1986
 P  G  K  L  M  I  S  I  Q  D  N  G  I  G  I  K  K
AAAACCTGAAGAAGGTGTTTGATAAGTTCTATCGCTGTCATACAGGTAATC  2037
 E  N  L  K  K  V  F  D  K  F  Y  R  V  H  T  G  N
TGCACGATGTAAAAGGTTTCGGTCTGGGACTGGCTTATGTGAAAAAGATTA  2088
 L  H  D  V  K  G  F  G  L  G  L  A  Y  V  K  K  I
TTCAGGATCATAAGGGAACCATCCGGGCGGAGAGTGAACTGATTGTAGGAA  2139
 I  Q  D  H  K  G  T  I  R  A  E  S  E  L  N  V  G
CTAAATTATTATTGCATTACCTTTATTAAAAAATGATTGATATGGACGAG   2190
 T  K  F  I  I  A  L  P  L  L  K  N  D  *
                                      M  I  D  M  D  E
AAACTGCGTATTTTATTATGCGAGGATGATGAAAATCTTGGCATGCTTTTA  2241
 K  L  R  I  L  L  C  E  D  D  E  N  L  G  M  L  L
```

FIG. 3E

```
             SspI
AGAGAATATTACAGGCGAAAGGTTACTCTGCTGAGTTGTATCCTGATGGA  2292
 R  E  Y  L  Q  A  K  G  Y  S  A  E  L  Y  P  D  G

GAAGCCGGATTTAAGGCTTTCCTGAAGAATAAATATGACTTGTGCGTGTTC  2343
 E  A  G  F  K  A  F  L  K  N  K  Y  D  L  C  V  F

GACGTGATGATGCCTAAGAAAGATGGTTTCACGCTGGCACAGGAGGTTCGT  2394
 D  V  M  M  P  K  K  D  G  F  T  L  A  Q  E  V  R

GCGGCCAACGCTGAAATTCCGATTATCTTCCTGACTGCAAAGACACTCAAG  2445
 A  A  N  A  E  I  P  I  I  F  L  T  A  K  T  L  K

GAGGATATTCTGGAAGGATTTAAGATTGGTGCGGATGATTACATCACCAAA  2496
 E  D  I  L  E  G  F  K  I  G  A  D  D  Y  I  T  K

CCTTTCAGTATGGAAGAACTTACTTTCAGAATTGAAGCGATCCTGAGACGT  2547
 P  F  S  M  E  E  L  T  F  Y  I  E  A  I  L  R  R

GTTCGTGGAAAAGAACAAAAGCAGATTCTGGCTATCGGTGACAAACAACTAAG  2598
 V  R  G  K  K  N  K  E  S  N  I  Y  K  I  G  K  F

ACGTTTGATACACAAAAGCAGATTCTGGCTATCGGTGACAAACAACTAAG  2649
 T  F  D  T  Q  K  Q  I  L  A  I  G  D  K  Q  T  K
           StyI
CTGACTACCAAGGAATCGGAATTGCTGGGATTGCTGTGTGCACATGCCAAC  2700
 L  T  T  K  E  S  E  L  L  G  L  L  C  A  H  A  N
```

FIG. 3F

```
GAGATTTGCAGCGTGACTTTGCTTTGAAGACTATCTGGATTGATGATAAC    2751
 E  I  L  Q  R  D  F  A  L  K  T  I  W  I  D  D  N
TATTTCAATGCCCGTAGTATGGACGTATATATCACCAAACTVCGTAAGCAC    2802
 Y  F  N  A  R  S  M  D  V  Y  I  T  K  L  R  K  H
CTGAAGGATGATGATTCGATTGAGATTATCAACATCCACGGAAAAGGTTAC    2853
 L  K  D  D  D  S  I  E  I  I  N  I  H  G  K  G  Y
AAGTTGATTACCCCCCGAACCCGGAATCATAATGGAGAGGGGGATATACAGAA    2904
 K  L  I  T  P  E  P  E  S  *
ATAAAAAGCCGGAAACATTCGTTTTCCGGCTTTTTATTTCTGTTGAAA    2955
SspI
ATATTAATCCGCAATTCTTTTATTGATCGCAATGTAAGAAATGAGTCCGAG    3006
```

```
          *                    *                    *  *  *          *   *
RprX   NMTHEFKTPIS  [98]  EMHITNVIFNLMDNA  [26]  IQDNGIGIKY  [23]  KGFGLGLAYV
CpxA   DISHELRTPLT  [91]  PNALESALENIVRNA  [22]  VDDDGPGVSP  [21]  GGTGPGPAIV
PhoR   NVSHELRTPLT  [94]  EDQLRSAISNLVYNA  [24]  VEDNGPGIAP  [21]  GGSGLGLSIA
CheA   RAAHSIKGGAG  [248] PEKTLEAGKNVVGNL  [14]  VTDDGAGLNT  [41]  SGRGVGMDVV
VirA   GIAHEFNNILG  [91]  PLELQQVLINICKNA  [39]  ISDNGGGIPE  [17]  GGTGLGLASV
NtrB   MLAHEIKNPLS  [89]  QDQLIQVFLNLVKNA  [41]  VKDNGSGVPE  [15]  TGSGLGLALV
```

```
            *                                                                               *
RprY   MIDMDEKLRILLCEDDENLGMLLREYLQAKGY SAELYPDGEAGFKAFLKNKYDLCVEDVMMPKKDG
OmpR   MQENYKNLVVDDDMRLRALLERYLTEQGF    QVRSVANAEQMDRLLTRESFHLMVLDLMLPGEDG
VirG   <EPLKHVLLVDDDVAMRHLLIEYLTIHAF    KVTAVADSTQFTRVLSSATVDVVVVDLNLGREDG
NR_I   MPAGSILVADDDTAIRTVLNQALSRAGY     EVRLTGNAATLWRWVSQGEGDLVITDVVMPDENA
PhoB   MARRILVVEDEAPIREMVCFVLEQNGF      QPVEAEDYDSAVNQLNEPWPDLILLDWMLPGGSG
SpoOF  MMNEKILIVDDQYGIRILLNEVENKEGY     QTFQAANGLQALDIVTKERPDLVLLDMKIPGMDG
CheY   MADKELKFLVVDDFSTMRRIVRNLLKELGFNNVEEAEDGVDALNKLQAGGFGPIISDWNMPNMDG
                                                            *
RprY   ETLAQEVRAANA    EIPIIFLTA KTLKEDILEGFKIGADDYITKPFSMEELTFRIEAILRRVRG>
OmpR   LSICRRLRSQSN    PMPIIMVTA KGEEVDRIVGLEIGADDYIPKPFNPRELLARIRPVLRRQAN>
VirG   LEIVRNL AAKS    DIPIILISGDRLEETDKVVALELGASDFIAKPFSIREFLARIRVALRVPRN>
NR_I   EDLLPRIKKMRP    NLPVIVMSA QNTFMTAIRPSERGAYEYLPKFDLKELITIVGRALAEPKE>
PhoB   IQEIKHLKRESMTRDIPVVMLTA  RGEEEDRVRGLETGADDYITKPFSPKELVARIKAVMRRISP>
SpoOF  IEILKRMKVIDE    NIRVIMTA  YGELDMIQESKELGALTHFAKPFDIDEIRDAVKKYLPLKSN
CHEY   LELLKTIRADSAMSALPVLMVTA  EAKKENIIAAAQAGASGYVVKPFTAATLEEKLNKIFEKLGM
```

CLONING AND IDENTIFICATION OF A TWO COMPONENT SIGNAL TRANSDUCING REGULATORY SYSTEM FROM *BACTEROIDES FRAGILIS*

FIELD OF THE INVENTION

This invention relates to a purified isolated DNA fragment of *Bacteroides fragilis* comprising a sequence for an operon containing two genes designated rprX and rprY. These genes encode two signal transducing regulatory proteins designated RprX and RprY. This invention further relates to the proteins RprX and RprY encoded by the operon.

BACKGROUND OF THE INVENTION

All cells are able to monitor and make appropriate adaptive responses to changes in their environment. Such adaptive responses in bacteria are often regulated by a multi-component signal transducing system. When exposed to the appropriate stimuli, a sensory receptor, generally an inner membrane protein, is activated to autophosphorylate a histidine residue. This high energy phosphate is transferred from the histidine to an aspartate residue on the second protein in the regulatory cascade, the regulatory response protein. It is the phosphorylated regulatory response protein that then mediates the adaptive response either by interacting with DNA, altering transcription, or with a specific protein(s), altering its activity. In addition to regulation at the level of phosphorylation, the amount of phosphorylated regulatory response protein is further controlled by associated phosphatases.

Regulatory systems of this nature have been identified in over twelve diverse bacterial genera and have been found to regulate a variety of cellular processes including virulence and pathogenic determinants. (For a review see Bibliography entries 1,2). In *Escherichia coli* (*E. coli*), it is predicted that there may be 50 different pairs of signal transducing proteins. Some of these pairs include CheY, CheA and CheB, which are involved in the gliding versus tumbling response of bacteria in chemotaxis; PhoR and PhoB, which regulate phosphorus assimilation; and EnvZ and OmpR, which regulate outer membrane porin protein expression (2,3,4,5,6).

*Bacteroides fragilis* is the major anaerobic bacterium comprising the bowel flora of man. *Bacteroides fragilis* is also one of the major anaerobic bacteria isolated from anaerobic or mixed infections. As such, this bacterium produces various virulence factors which are involved in colonization and invasion of the organism. These factors include activities such as a nuraminidase.

This invention relates to the cloning and identification of a pair of signal transducing regulatory proteins cloned from *Bacteroides fragilis*, as well as to the phenotypes that expression of the regulatory proteins imparts upon *E. coli*.

SUMMARY OF THE INVENTION

A DNA fragment is cloned from *Bacteroides fragilis* that bestows low level tetracycline resistance to *E. coli* strains harboring the cloned fragment on a multi-copy plasmid. The tetracycline resistance determinant is localized to a 4.3 kilobase (kb) BglII-PstI subfragment of the original clone. DNA sequence analysis of this purified isolated fragment reveals that it contains an operon encoding two proteins, one of 519 amino acids, designated RprX, and a second of 233 or 236 amino acids, designated RprY. Protein sequence analysis reveals that the two proteins share sequence identity with a family of multi-component signal transducing regulatory proteins identified from many diverse bacterial genera.

RprX shares identity with the first component of the regulatory system, the histidine protein kinase receptor (for example: CpxA, PhoR, and CheA). RprY shares identity with the second member of the regulatory protein pair, the regulatory response protein, (for example: OmpR, PhoB, VirG, SpoOF and NtrC). Expression of these RprX and RprY proteins from a multi-copy plasmid vector in *E. coli* results in a decrease in the level of the outer membrane porin protein OmpF and an increase in the level of the outer membrane porin protein OmpC. The decrease in OmpF levels correlates with and may be the cause of the increase in tetracycline resistance.

Regulation of the levels of OmpF and OmpC is normally controlled by a multi-component signal transducing regulatory pair of proteins, EnvZ and OmpR. The effect RprX and RprY have on OmpF expression is shown to be mediated at the level of transcription. Thus, RprX and RprY are affecting the normal regulation of OmpF by OmpR and EnvZ.

BRIEF DESCRIPTION OF THE DRAWINGS

FIGS. 3A–3F depict the DNA sequence of the BglII-PstI fragment from nucleotide 356 to 3006. This corresponds to the nucleotides numbered 1 to 2651 in SEQ ID NO. 1. Below the sequence is the translated amino acid sequence of the two large open reading frames encoding RprX and RprY. The first ATG codon of each open reading frame is underlined. The * indicates the stop codon terminating each polypeptide. Potential −10, −35, and Shine-Dalgarno (S-D) sequences are indicated above their respective sequences. The two copies of a 12 base pair repeated sequence upstream of the RprX coding sequence are underlined. The 24 base pair inverted repeat at the end of the coding sequence for RprY is underlined. The location of the IS1 insertion within RprX is indicated with an arrowhead between nucleotides 2043 and 2044 (numbered 1688 and 1689 in SEQ ID NO. 1). The HindIII site (nucleotides 1037–1042 (SEQ ID NO.1 682–687)) and two SspI sites (nucleotides 2246–2251 (SEQ ID NO. 1 1891–1896) and nucleotides 2955–2960 (SEQ ID NO. 1 2600–2605)) are indicated above the respective cleavage recognition sequences.

FIG. 4 depicts a comparison of the conserved amino acid sequence within the homologous domains of several histidine kinase protein kinase proteins to RprX (SEQ ID NOS. 30-33, from relevant portions of SEQ ID NO.2). Totally conserved amino acids are indicated with an * in the top line. Among these conserved residues is the proposed phosphorylated histidine (1,7,8). The numbers in brackets indicate the number of residues separating the conserved regions. Protein sequences are from the following sources: CpxA from *E. coli* (SEQ ID NOS. 4-7)(9), PhoR from *E. coli* (SEQ ID NOS. 8-11)(4), CheA from *E. coli* (SEQ ID NOS. 12-15)(6), VirA from *Agrobacterium tumefaciens* (SEQ ID NOS. 16-19)(10), and NtrB from *Bradyrhizobium parasponia* (SEQ ID NOS. 20-23)(11).

FIG. 5 depicts a comparison of the conserved amino acid sequence within the homologous N-terminal domains of several regulatory response proteins to RprY (SEQ ID NOS. 34-38, from relevant portions of SEQ ID NO.3). The three highly conserved residues are depicted with an * in the top line. The second conserved aspartate has been demonstrated to be the phosphorylated residue for several of the regulatory response proteins (7,8). Residues corresponding to those which comprise the hydrophobic core of CheY are underlined (1,2). Protein sequences are from the following sources: OmpR from *E. coli* (SEQ ID NO. 24)(3), VirG from *Agrobacterium tumefaciens* (SEQ ID NO. 25)(12), NtrC from *Bradyrhizobium parasponia* (SEQ ID NO. 26)(11), PhoB from *E. coli* (SEQ ID NO. 27)(4), SpoOF from *Bacillus subtilis* (SEQ ID NO. 28)(13), and CheY from *E. coli* (SEQ ID NO. 29) (1,14).

DETAILED DESCRIPTION OF THE INVENTION

Figure 1A:
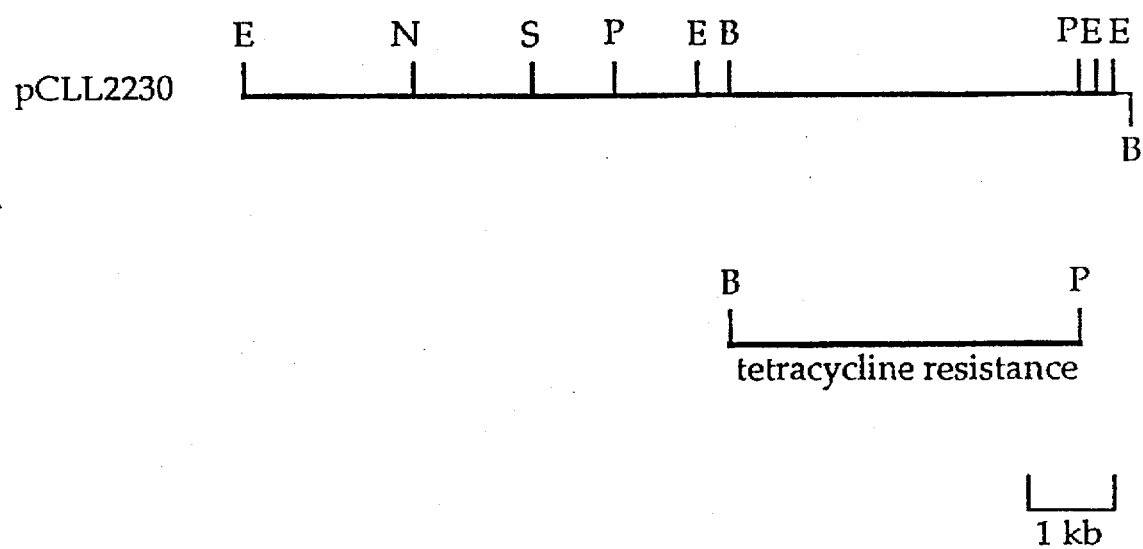
FIGS. 1A and 1B depict the restriction endonuclease map of the EcoRI fragments of the cloned plasmid pCLL2230 and localization of the tetracycline resistance locus. Panel A depicts the restriction endonuclease cleavage sites within the cloned DNA, which are shown above the line. The BglII restriction site shown below the line is part of the vector polylinker. The tetracycline resistance locus lies within the BglII-PstI fragment shown. Panel B depicts plasmids harboring subfragments of the original clone and indicates their ability to confer tetracycline resistance. Restriction enzyme abbreviations: B, BglII; E, EcoRI; N, NdeI; P, PstI; and S, StuI.

The purified isolated DNA fragment of *B. fragilis* of this invention, which comprises a sequence for an operon containing two genes designated rprX and rprY, is obtained from an existing clone bank of *B. fragilis* DNA. A total chromosomal clone bank of *B. fragilis* DNA had been created previously (15,16) by digesting *B. fragilis* chromosomal DNA with EcoRI, cloning into pCLL2300 (a kanamycin resistance conferring vector), and transforming in *E. coli* selecting for kanamycin resistance. The original clone bank is constructed in *E. coli* DH5α (F-, endA1, hsdR17 ($r_k^-$,$m_k^+$), supE44, thi-1, recA1, gyrA96, relA1Δ (argF-lacZYA)U169, Φ80dlacZΔM15) (Bethesda Research Laboratories, Inc., Gaithersburg, Md.). Unless otherwise indicated, all isolates studied are derivatives of *E. coli* DH5α.

Tetracycline resistance conferring plasmids are identified by plating approximately $10^5$-$10^6$ cells from the pool of 20,000 transformed colonies onto kanamycin and tetracycline (3 μg/ml) containing plates and incubating under anaerobic conditions at 37° C. Tetracycline resistance colonies appear as small colonies after two to three days of incubation.

All experiments are performed using LB medium (17) supplemented, when required, with kanamycin (25 μg/ml) and tetracycline. All cultures are incubated at 37° C. Anaerobic growth conditions are achieved with the use of a BBL GasPak jar (Becton Dickinson and Co., Cockeysville, Md.). Several hundred small colonies are visible. Plasmid DNA is isolated from several of these tetracycline resistant colonies and the DNA insert is characterized.

Endonuclease restriction analysis is then performed. Restriction enzymes, calf-intestinal phosphatase and T4 DNA ligase are obtained from Boehringer Mannheim Biochemicals (Indianapolis, Ind.) and used according to the manufacturer's instructions (18). Standard recombinant DNA techniques are performed according to the protocols in Sambrook et al. (18).

This analysis reveals that all of the plasmids examined harbor two large EcoRI fragments, each approximately 5 kb in size. DNA sequence analysis subsequently reveals a third fragment of 75 base pairs (the EcoRI-EcoRI fragment shown at the right side of pCLL2230 in FIG. 1A). The identification of the same size EcoRI fragments in all the plasmids studied suggests that the tetracycline resistant colonies are siblings, originating from one initial transformed cell. The plasmids are transformed into a fresh background and found to be capable of conferring low level tetracycline resistance, suggesting that a tetracycline resistance determinant is cloned on the plasmid.

One plasmid, designated pCLL2230, is selected for further studies. This plasmid contains two EcoRI fragments, each approximately 5 kb in length (FIG. 1A). Southern hybridization analysis using sequences from the two EcoRI cloned fragments to probe *B. fragilis* DNA indicates that both EcoRI fragments are of *B. fragilis* origin and are not contiguous on the chromosome.

Figure 1B:
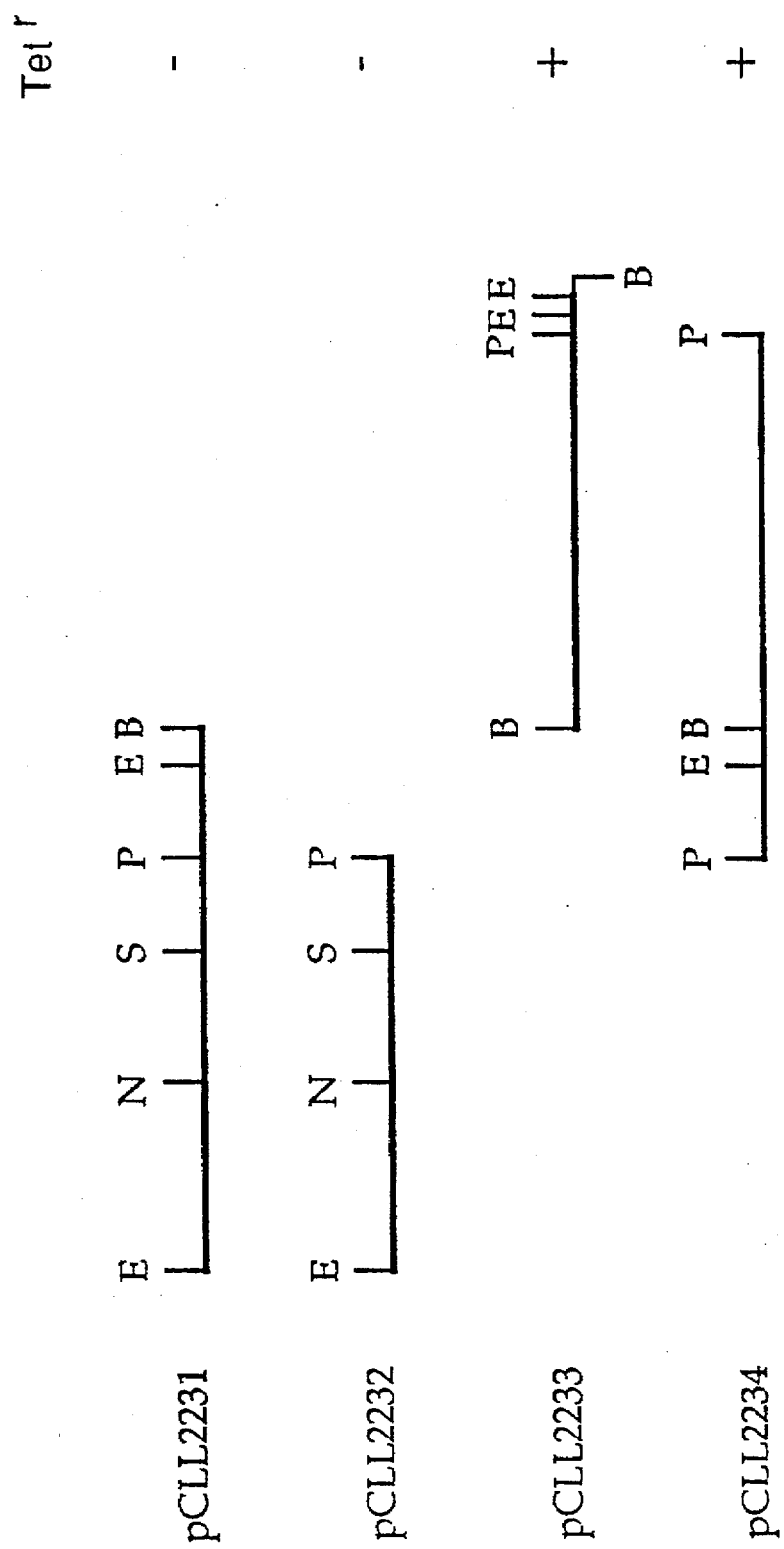

To facilitate localization of the putative tetracycline resistance determinant, a restriction map is generated (FIG. 1). Utilizing this map, various regions of the cloned DNA fragments are selected for subcloning and determination of their ability to confer tetracycline resistance (FIG. 1). From this analysis, the low level tetracycline resistance locus is localized to a 4.2 kb BglII-PstI fragment, which is a subfragment of the slightly smaller of the two approximately 5 kb EcoRI fragments.

*E. coli* transformed with a multi-copy plasmid harboring the tetracycline resistance locus on either the BglII fragment (pCLL2233) or the slightly larger PstI fragment (pCLL2234) (FIG. 1B) grows slowly. When grown on LB medium, isolates harboring pCLL2233 have a doubling time of 105 minutes versus 45 minutes for an isogenic strain harboring the vector with no insert. Cells harboring pCLL2233 or pCLL2234 also form small colonies, requiring two days at 37° C. to form normal sized colonies on rich medium. The tetracycline resistance, although detectable, is difficult to score when cells harbor these subfragments of the original clone. The resistance is also unstable and easily lost, in the absence of selection, without concomitant loss of the plasmid.

The entire BglII fragment (pCLL2233) is sequenced to aid in the identification of the mechanism of the tetracycline resistance conferred by the fragment. To accomplish this, the BglII fragment is subcloned and both DNA strands are sequenced. DNA sequence analysis is performed using the Sanger dideoxy method (19) with the Sequenase™ kit (United States Biochemical, Cleveland, Ohio) used according to the manufacturer's directions.

Figure 2:
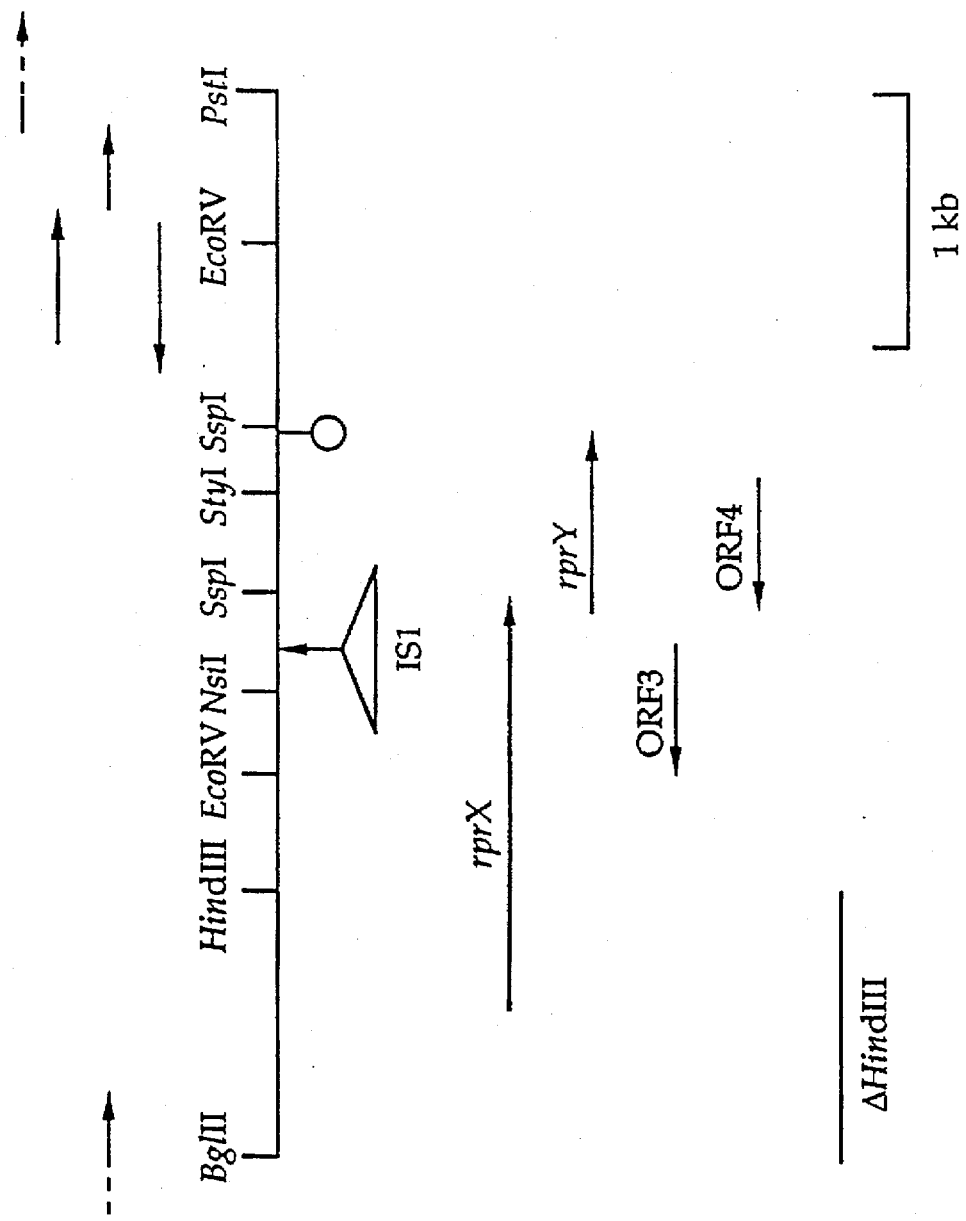
FIG. 2 depicts the open reading frames and restriction endonuclease sites identified within the BglII-PstI fragment. Shown below the depicted BglII-PstI fragment are the location and direction of transcription of the four open reading frames (ORFs) discussed in the specification. The arrows shown above the line represent other potential ORFs and their direction of transcription. The lollypop depicts the location of the 24 base pair inverted repeat. The location of the IS1 insertion within rprX is indicated. The DNA deleted in the BglII-HindIII deletion (ΔHindIII) is also indicated.

To facilitate sequencing, the BglII fragment is subcloned. A BglII-HindIII, a HindIII-HindIII and a BglII-NsiI fragment are cloned into pUC118 and pUC119 (20) (FIG. 2). One of the HindIII restriction sites is part of the polylinker into which the BglII fragment is cloned. Sequencing is performed on either single stranded DNA, prepared using the helper phage M13K07 (20), or double stranded plasmid DNA, prepared by the boiling mini prep method (18).

Both strands of the BglII-HindIII and HindIII-HindIII fragments are sequenced in their entirety. The BglII-NsiI fragment is sequenced in the region corresponding to the HindIII junction of the other two fragments. The primers utilized are the M13-40 universal primer (New England Biolabs, Beverly, Mass.) and additional synthetic oligonucleotides spaced 150-250 bases apart and complementary to determined DNA sequence. DNA sequence analysis, translation, protein data base searches, and protein sequence comparisons are performed using the DNA Star™ (DNA Star Inc., London, England) computer program.

The DNA sequence shows several interesting features, as depicted in FIGS. 2 and 3. There are two open reading frames (ORFs): The first ORF encodes a protein of 519 amino acids. The second ORF encodes a smaller protein of 233 or 236 amino acids (there are two potential ATG initiation codons for this protein, resulting in a protein of 233 or 236 amino acids depending on which ATG is utilized to initiate translation). From the DNA sequence, the two genes appear to be coordinately expressed from the same promoter and, therefore, compose an operon.

Due to their homology with known regulatory proteins (see below), the 519 and 233 or 236 amino acid proteins are designated RprX and RprY (Regulatory protein X and Y), respectively. Their respective genes are designated rprX and rprY. The coding sequences of rprX and rprY overlap by five base pairs (nucleotides 2173-2177 in FIG. 3; numbered 1818-1822 in SEQ ID NO. 1) if the first ATG in rprY is utilized as the initiation codon. Alternatively, a second ATG codon, located five base pairs downstream from the stop codon for rprX, could also function as the translation initiation codon for rprY.

The locations of the two ORFs within the BglII-PstI fragment are as follows: FIG. 3 depicts the operon and flanking regions as nucleotides numbered 356-3006 (numbered 1-2651 in SEQ ID NO. 1). The rprX gene is nucleotides 621-2177 in FIG. 3 (numbered 266-1822 within SEQ ID NO. 1). If the first possible ATG in rprY is the initiation codon, then the rprY gene is nucleotides 2173-2880 in FIG. 3 (numbered 1818-2525 within SEQ ID NO. 1). If the second possible ATG in rprY is the initiation codon, then the rprY gene is nucleotides 2182-2880 in FIG. 3 (numbered 1827-2525 within SEQ ID NO. 1).

Preceding the rprX coding sequence are several potential −10 and −35 sequences, based upon E. coli consensus sequences (21), and a potential Shine-Dalgarno sequence, based upon the B. fragilis 16S rRNA sequence (22). No potential Shine-Dalgarno sequence is identified upstream of either ATG codon of the rprY coding sequence.

Within the sequences directly upstream of the rprX coding sequence is a tandem repeat of 12 base pairs. Immediately following the rprY coding sequence is a 24 base pair perfect inverted repeat separated by four base pairs that could function in transcription termination (23). Within the 1.5 kb downstream of the operon, there are several small ORFs encoding proteins of 81 to 169 amino acids. There are also ORFs extending beyond both ends of the DNA fragment. It is to be noted that within each of the rprX and rprY coding sequences is a small ORF, designated ORF3, encoding a protein of 170 amino acids, and ORF4, encoding a protein of 149 amino acids, respectively. These small ORFs are each in the same frame as the proteins encoded by rprX and rprY, but are transcribed from the opposite strand. There is no indication that ORF 3 and ORF 4 are functional.

The predicted protein sequences of both RprX and RprY are compared with the GenBank protein data base. RprX shares sequence identity with CpxA (26.9%), PhoR (20.4%), and CheA (18.6%), and weaker identity with VirA and NtrB. All of these proteins are histidine protein kinases and represent one component of a multi-component signal transducing regulatory system. The regions of greatest identity between proteins of this family are the histidine kinase domain, generally located near the carboxy terminal end of the protein, and the region surrounding the phosphorylated histidine residue. The amino acid sequence N-(then an intervening 15 to 45 residues)-DXGXG-(SEQ ID NO. 39) (then an intervening 20 to 50 residues)-GXG is conserved among all the histidine protein kinases (1,2,8). With the exception of CheA and FrzE (another histidine protein kinase protein), the proposed autophosphorylated histidine residue lies approximately 100 amino acids upstream of the conserved asparagine (1). RprX contains all of these features (FIG. 4).

RprY shares sequence identity with OmpR (32.6%), PhoB (28.7%), VirG (28.7%), SpoOF (27.7%), and NtrC (21.0%) and weaker identity with CheY, SpoOA, and several other regulatory response proteins. These proteins comprise the second protein of the multi-component signal transducing regulatory systems. The average homology among this class of proteins is 20-30%, with the strongest homology located in the amino terminal half of the protein (1,2). Within this region, there are three absolutely conserved amino acids: two aspartates, one being the phosphorylated aspartate, and a lysine (1,2,7,8). There are also several conserved stretches of hydrophobic amino acids (1,2). Both aspartates, the lysine and the hydrophobic regions are present within RprY (FIG. 5).

Thus, these amino acid sequence comparisons of RprX and RprY to other known proteins clearly reveal that the two proteins share strong sequence identity with a family of multi-component signal transducing regulatory proteins. Detailed analysis of the conserved amino acids and overall protein structure of the two proteins with other known regulatory proteins indicate that RprX and RprY contain all the features characteristic of known histidine protein kinases and regulatory response proteins, respectively. From these findings it is hypothesized that RprX and RprY represent two proteins that together form a pair of regulatory proteins. This is then tested by a series of characterization studies discussed below.

The signal transducing regulatory proteins RprX and RprY of this invention are expressed using established recombinant DNA methods. Suitable host organisms include bacteria, viruses, yeast, insect or mammalian cell lines, as well as other conventional organisms. For example, the E. coli strain DH5α is transfected with either of the multi-copy plasmids designated pCLL2230 or pCLL2233, which include the rprX and rprY genes. The host cell is then cultured under conditions which permit the expression of the RprX and RprY proteins.

Samples of an *E. coli* strain DH5α containing the multicopy plasmid designated pCLL2230 (which includes the rprX and rprY genes of this invention) were deposited by Applicant on Feb. 22, 1993, with the American Type Culture Collection, 12301 Parklawn Drive, Rockville, Md. 20852, U.S.A., and have been assigned ATCC accession number 69246.

The present invention further comprises DNA sequences which, by virtue of the redundancy of the genetic code, are biologically equivalent to the DNA sequences described specifically herein which encode for the regulatory proteins, that is, these other DNA sequences are characterized by nucleotide sequences which differ from those set forth herein, but which encode regulatory proteins having the same amino acid sequences as those encoded by the DNA sequences set forth herein.

In particular, the invention contemplates those purified isolated DNA fragments containing sequences encoding the regulatory proteins which are sufficiently duplicative of the sequences of the operon contained within SEQ ID NO. 1, so as to permit hybridization therewith under standard high stringency Southern hybridization conditions, such as those described in Sambrook et al. (18), as well as the biologically active regulatory proteins produced thereby.

This invention also comprises DNA sequences which encode amino acid sequences which differ from those of the described regulatory proteins as set forth in SEQ ID NOS. 2 and 3, but which are the biological equivalent to those described for the regulatory proteins. Such amino acid sequences may be said to be biologically equivalent to those of the regulatory proteins if their sequences differ only by minor deletions from or conservative substitutions to the regulatory proteins, such that the tertiary configurations of the sequences are essentially unchanged from those of the regulatory proteins.

For example, a codon for the amino acid alanine, a hydrophobic amino acid, may be substituted by a codon encoding another less hydrophobic residue, such as valine, leucine or isoleucine. Similarly, changes which result in substitution of one negatively charged residue for another, such as aspartic acid for glutamic acid, or one positively charged residue for another, such as lysine for arginine, as well as changes based on similarities of residues in their hydropathic index, can also be expected to produce a biologically equivalent product. Nucleotide changes which result in alteration of the N-terminal or C-terminal portions of the molecule would also not be expected to alter the activity of the regulatory proteins. It may also be desirable to eliminiate one or more of the cysteines present in the sequence, as the presence of cysteines may result in the undesirable formation of multimers when the protein is produced recombinantly, thereby complicating the purification and crystallization processes. Each of the proposed modifications is well within the routine skill in the art, as is determination of retention of activity of the encoded regulatory proteins. Therefore, where the terms "gene", "DNA encoding sequence" and "sequence" are used in either the specification or the claims, each will be understood to encompass all such modifications and variations which result in the production of a biologically equivalent regulatory protein.

Figure 6:
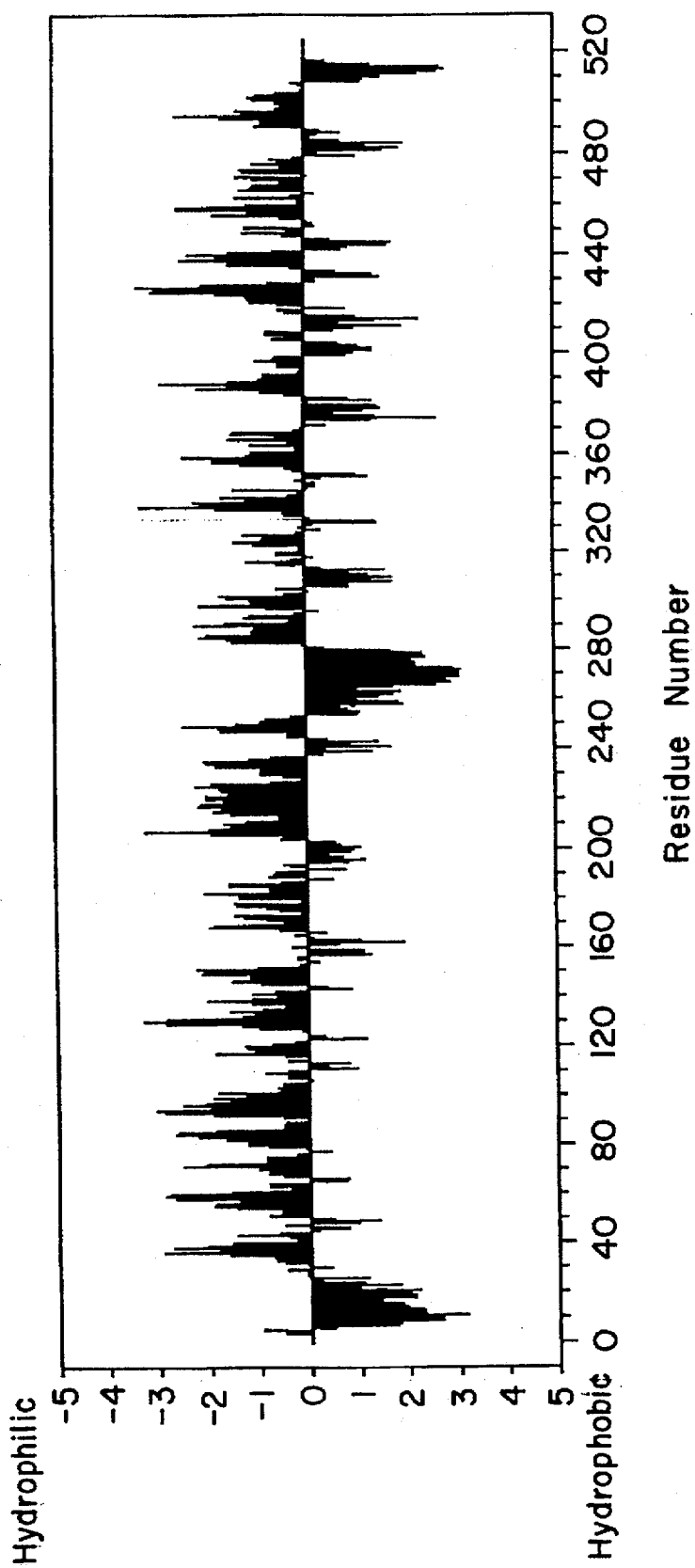
FIG. 6 depicts a hydropathy plot of RprX.

A series of characterization studies is carried out regarding the structure and function of RprX and RprY. First, the hydrophobicity of RprX is analyzed. Many of the signal transducing proteins similar to RprX are inner membrane proteins. They contain two membrane spanning regions, a periplasmic domain containing the sensory receptor and a carboxy terminal cytoplasmic domain harboring the histidine protein kinase activity, as well as the autophosphorylated histidine residue. A hydropathy plot is performed on RprX to predict potential membrane spanning and soluble domains utilizing the algorithms of Kyte and Doolittle (24) (FIG. 6). Interpretation of the plot leads to the prediction that there are two potential membrane spanning regions: one between the amino acids 4 and 26, and a second between amino acids 252 and 281. The intervening regions between these segments are hydrophilic and predicted to be soluble domains, with the more amino terminal domain residing in the periplasm and the carboxy terminal domain residing in the cytoplasm. This is in agreement with the structure of other known histidine protein kinase receptors and the protein sequence alignment data.

Next, disruption of the rprX and rprY coding sequences is studied. *E. coli* cells harboring the BglII DNA fragment encoding RprX and RprY display low level tetracycline resistance, grow slowly and form small colonies on rich media. Both the slow growth/small colony phenotype and the ability to confer tetracycline resistance are dependent upon expression of RprY and perhaps RprX.

Analysis of the initial DNA sequence of the BglII fragment indicates that sometime during subcloning and propagation of the plasmid for sequencing, an insertion sequence element designated IS1 had been inserted within the coding sequence of rprX. An insertion element is a small transposable element capable of inserting, more or less randomly, into DNA.

The location of the IS1 insertion is depicted in FIGS. 2 and 3. Cells transformed with pCLL2233 containing the IS1 insertion no longer exhibit the slow growth/small colony phenotype or low level tetracycline resistance of cells harboring pCLL2233, carrying a wild-type BglII fragment.

Thus, it appears that expression of RprX and/or RprY is responsible for the phenotypes associated with harboring the BglII DNA fragment. It is observed that, when pCLL2233 plasmid DNA is used to transform *E. coli* cells, between 1% and up to 50% of the transformed colonies are of normal size while the remainder are small or pin-point sized colonies. If expression of RprX and/or RprY is responsible for the small colony phenotype, these larger sized colony transformants might contain pCLL2233 plasmids in which the rprXY operon is disrupted. This could be easily accomplished by the insertion of a DNA sequence (i.e. an insertion sequence (IS) element) within the rprXY operon.

Seven independent large colony forming pCLL2233 transformed isolates are examined. Large colony variants are obtained by growing pCLL2233 harboring cells overnight, isolating plasmid DNA from them, transforming the DNA into a fresh background, and identifying large colony forming transformants. Plasmid DNA is obtained from these large colony forming isolates and subjected to restriction analysis. Digestion of pCLL2233 with BglII and SspI results in the formation of three subfragments comprising the cloned BglII fragment, a 2.2 kb fragment containing rprX and less than 80 base pairs of rprY coding sequence, a 0.7 kb fragment containing the remainder of the rprY coding sequence plus 75 bp downstream of the rprY coding sequence including the 24 bp inverted repeat, and a 1.5 kb fragment comprising the remainder of the BglII fragment (FIG. 2). The subfragments are visualized by an ethidium bromide stained agarose gel.

Figure 7:
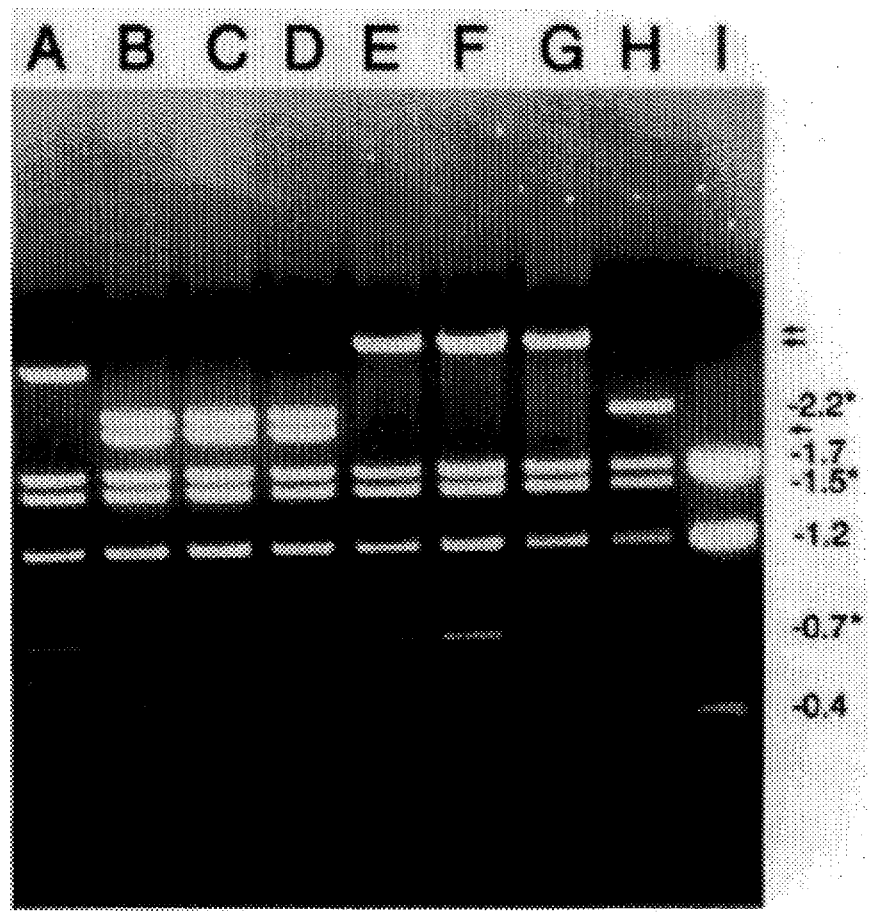
FIG. 7 depicts an ethidium bromide stained agarose gel of BglII-SspI restricted plasmid DNA isolated from small and large colony forming pCLL2233 containing cells. Lanes A-G, plasmid isolated from 7 independent large colony formers (see text); lane H, plasmid isolated from a small colony former; lane I, pCLL2300 vector plasmid. Denoted to the right are the band position and size of the vector and insert fragments. The bands representing fragments of the insert DNA are indicated with an *. The arrowheads indicate the position of new bands identified among lanes A-G.

When plasmid DNA from the seven large colony forming isolates is examined, either the 2.2 or 0.7 kb band is lost and a new, slower migrating band appears (FIG. 7). Four of the plasmids examined show a loss of the 2.2 kb fragment (lanes A, E, F, and G, FIG. 7). The 0.7 kb fragment is missing from the other three plasmids (lanes B,C, and D, FIG. 7). *E. coli* transformed with any of these seven plasmids no longer exhibits the small colony phenotype or increased tetracycline resistance.

These results indicate that DNA insertions within the 2.2 kb BglII-SspI fragment, one of which is known to lie within the coding sequence for RprX, or the 0.7 kb SspI-SspI fragment, 90% of which is RprY coding sequence, eliminate all the observed phenotypes. This strongly suggests that RprY and perhaps RprX expression is responsible for the observed phenotypes.

Studies utilizing a DNA insertion within the 2.2 kb fragment use the original IS1 insertion within the rprX coding sequence. The exact location of the DNA insertions within the 0.7 kb fragment is not determined.

Because the only ORFs within the 0.7 kb fragment are rprY and ORF4, and their coding sequence comprises up to 90% of the 0.7 kb DNA sequence, any insertion within this fragment is likely to disrupt one or both of these two ORFs. However, it cannot be ruled out from these DNA insertions alone that one or both of the two small ORFs, ORF3 or ORF4, whose coding sequences overlap those of RprX and RprY, respectively, are responsible for the observed phenotypes.

Therefore, in addition to the DNA insertions, a construct deleting the upstream and amino terminal coding sequence of rprX is created. DNA sequences between the BglII and the HindIII restriction sites (ΔHindIII) (FIG. 2) are removed. This deletion does not disrupt the upstream or coding sequences of ORF3 or ORF4, but does delete the upstream DNA and 5' coding region of rprX. *E. coli* transformed with pCLL2233 ΔHindIII displays normal growth characteristics and exhibits no increased tetracycline resistance. Therefore, the deletion results in the elimination of expression of RprX and RprY and, consequently, the elimination of all phenotypes associated with harboring the BglII fragment.

This indicates that expression of RprY and perhaps RprX, and not the polypeptides encoded by ORF3 and ORF4, is responsible for the observed phenotypes. Since rprX and rprY form an operon, disruption of rprX would have a polar effect on the expression of rprY. Thus, it cannot be determined if RprX contributes to the observed phenotypes. Expression of RprY alone may be sufficient to elicit the observed phenotypes.

Next, the effect of the cloned BglII fragment on the level of OmpF and OmpC in *E. coli* is studied. The observation that the slow growth/small colony phenotype could be eliminated by DNA insertions within rprX and rprY indicates that expression of one or both of the Rpr proteins has a negative effect on cell growth. Among the different types of proteins whose expression is regulated by a multicomponent signal transducing regulatory system are outer membrane proteins, for example, the porin proteins OmpF and OmpC by the EnvZ/OmpR regulatory system, and PhoE by the PhoB/PhoR regulatory system (1). Therefore, the possibility that the *B. fragilis* regulatory proteins may be affecting the expression of *E. coli* outer membrane proteins is investigated.

A series of *E. coli* DH5α cells is transformed with, respectively, pCLL2300 (labelled vector in FIG. 8), pCLL2233 two independent transformed isolates (labelled isolate 1 and isolate 2), pCLL2233 with the IS1 element within the 2.2 kb BglII-SspI fragment (labelled IS 2.2), pCLL2233 with a DNA insertion within the 0.7 kb SspI fragment (labelled IS 0.7), or pCLL2233 with the ΔHindIII deletion (labelled ΔHindIII).

These cells are fractionated and SDS polyacrylamide gel electrophoresis is performed as follows: Overnight cultures of the appropriate isolates are diluted 1:50 into 200 mls of fresh LB medium. Cultures are grown with aeration at 37° C. to a final $OD_{550}$ of 0.6–0.7. Cells are harvested, washed once with 10 mM HEPES, pH 7.4, and resuspended in 2.5 mls of 10mM HEPES, pH 7.4. The cells are broken by two passes through a French press at 15,000 psi. After breaking, $MgCl_2$ is added to 1 mM. One tenth ml of lysed cells is removed, representing the whole cell fraction. The remainder is centrifuged for 30 minutes at 20,000×g at 4° C.

The supernatant, soluble fraction is decanted and saved. The pellet is resuspended in 5 mls of water and centrifuged again for 30 minutes at 20,000×g at 4° C. The final pellet, sacculas or outer membrane prep, is resuspended in 2.4 mls 10 mM HEPES, pH 7.4. Each fraction is mixed with an equal volume of 2× sample buffer boiled for five minutes, loaded on a 10% polyacrylamide gel and electrophoresed as previously described (25). Utilizing these gel conditions (no urea), the OmpF and OmpC protein bands separate. The OmpC protein migrates faster and, therefore, appears below the OmpF band (see FIG. 8).

Figure 8:
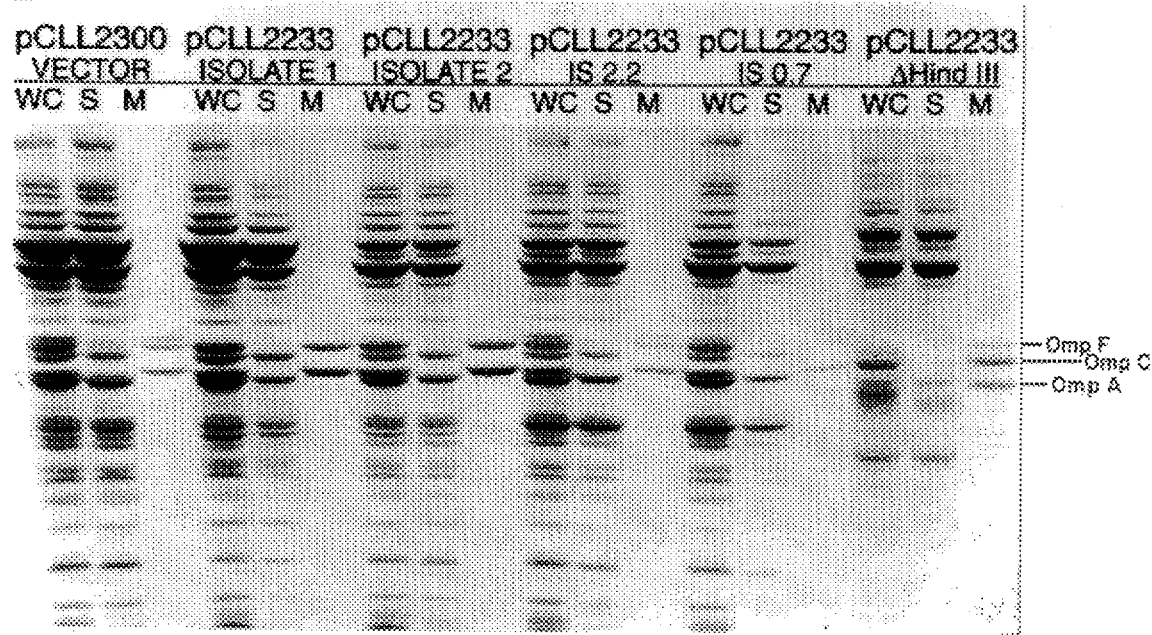
FIG. 8 depicts a Coomassie blue stained polyacrylamide gel of cellular fractions of DH5α harboring either pCLL2300 (vector); pCLL2233 two independent transformed isolates, isolate 1 and isolate 2; pCLL2233 containing the IS1 insertion known to reside within the coding sequence for RprX on the 2.2 kb BglII-SspI fragment, IS 2.2; pCLL2233 with a DNA insertion within the 0.7 kb SspI fragment, IS 0.7; or pCLL2233 containing the BglII-HindIII deletion, ΔHindIII. WC, whole cell lysate; S, soluble cell fraction; and M, outer membrane fraction. The positions of OmpF, OmpC, and OmpA are indicated.

It is observed that cells transformed with pCLL2300 (vector) contain nearly equal amounts of OmpF and OmpC in their outer membrane when grown on LB medium broth. In contrast, cells transformed with pCLL2233 contain little or no detectable OmpF in their outer membrane and show increased levels of OmpC under the same growth conditions. Disruption of rprX and/or rprY by DNA insertion, DNA insertions within the 2.2 kb or 0.7 kb fragments respectively, restores the levels of OmpF and OmpC to those of cells harboring vector alone. Deletion of the upstream and amino terminal coding sequences of rprX (ΔHindIII deletion) also restores the levels of OmpF and OmpC to those of cells harboring vector alone (FIG. 8). Immune precipitation of OmpF from cellular extracts of isolates harboring pCLL2300 (vector), pCLL2233 with a DNA insertion within the 2.2 kb or 0.7 kb fragments, or pCLL2233 with the ΔHindIII deletion reveals that all four isolates synthesize OmpF. In contrast, no OmpF can be detected by immune precipitation from cellular extracts of cells which harbor a known wild-type pCLL2233 plasmid.

Regulation of the outer membrane porin proteins OmpF and OmpC normally occurs at the level of transcription. Transcriptional regulation is coordinated through EnvZ and OmpR and correlates with the levels of OmpC and OmpF in the outer membrane. Since RprX and RprY appear to represent regulatory proteins of the same family as OmpR and EnvZ, it is of interest to determine if their effect on the amount of OmpF in the outer membrane is also mediated at the level of transcription. This is assessed by assaying the beta-galactosidase activity of an ompF-lacZ operon fusion harboring strain, MH513 (26), containing various RprX and RprY encoding plasmids.

In this MH513 strain, transcription of lacZ is under control of the ompF promoter, but translation is under control of the lacZ promoter. Therefore, translation of lacZ is independent of ompF regulation. In this situation, beta-galactosidase levels reflect the relative abundance of the transcript, and thus the level of transcription.

In this beta-galactosidase assay, MH513 (26), ompF-lacZ operon fusion, and MH225 (26), OmpC-lacZ operon fusion, C600 (27, New England Biolabs) cells are transformed with pCLL2300 and derivatives of pCLL2233. Two ml cultures of LB medium broth are inoculated with a transformed colony and incubated at 37° C. overnight. The overnight cultures are diluted 1:4 to 1:50 into 2 mls of LB medium and incubated for several hours at 37° C. When the cultures reach mid log phase, the cells are harvested and resuspended in two mls of Z buffer (17). One ml is removed for determination of the $OD_{600}$. The remaining cells are mixed with one drop of 1% SDS and two drops of $CHCl_3$. A 12–100 µl aliquot of the cell suspension is added to microtiter plate wells and the final volume adjusted to 200 µl with Z buffer. The reaction is initiated by the addition of 50 µl of 10 mg/ml ONPG (orthonitrophenyl beta-D-galactopyranoside) in Z buffer without added beta-mercaptoethanol. The absorbance is monitored at 405 nm using a Molecular Devices (Menlo Park, Calif.) microplate reader. The formula used to calculate the relative level of enzymatic activity is:

$$\frac{\Delta A_{405}/\Delta \text{Min}}{(OD_{600}) \text{ (ml of cell suspension added to the reaction)}}$$

The results of the beta-galactosidase assay are that, when MH513 harbors either the vector plasmid, pCLL2300, or any of the three plasmids on which rprY and/or rprX are inactivated, pCLL2233 IS 0.7, pCLL2233 IS 2.2, or pCLL2233 ΔHindIII, equivalent levels of beta-galactosidase enzymatic activity are detected. However, isolates harboring pCLL2233 containing wild-type rprX and rprY genes show an 8–10 fold or greater decrease in the level of beta-galactosidase enzymatic activity. One culture has no detectable beta-galactosidase activity.

Similar studies with a strain harboring an ompC-lacZ operon fusion cannot be interpreted due to the high instability of these cultures, perhaps a result of the stress resulting from their inability to compensate for the decrease in OmpF levels by synthesizing additional OmpC. As a control, studies of the effect of RprX and RprY expression on LacZ activity expressed from wild-type lacZ are investigated. The results show that there is only a less than 25% decrease in the level of enzymatic activity between extracts from cells harboring either the vector, pCLL2300, or any of the three plasmids containing an inactivated rprY or rprX gene and cells harboring plasmid pCLL2233 containing wild-type rprX and rprY genes.

The tetracycline resistance imparted upon E. coli harboring the cloned BglII fragment is not the result of any known mechanism of specific tetracycline resistance such as an efflux pump, ribosomal protection, or tetracycline inactivation (28). No DNA sequence homology between the tetracycline resistance imparting fragment and genes representing any of these mechanisms of resistance is identified. Instead, the resistance may be a secondary effect of the reduction in OmpF levels. Tetracycline resistance in gram negative bacteria can be greatly affected by changes in the outer membrane that alters its permeability. Decreases in the level of OmpF have been correlated with increases in the resistance to tetracyclines and other antibiotics (29,30). The tetracycline resistance observed here correlates with the reduction in the level of OmpF.

The effect of rprX and rprY expression on growth rates and colony size are not as easily explained. Elimination of OmpF alone has not been observed to have a dramatic effect on the growth rate when E. coli are grown in LB medium. The small colony phenotype may be the result of a more pleotrophic effect of rprY and/or rprX expression on cellular regulation. There are at least 20 known multi-component regulatory protein pairs in E. coli and there are predicted to be as many as 50 total pairs (1,2), regulating a plethora of cellular functions. Several studies have shown that these regulatory proteins can "crosstalk" (31,32). That is, the histidine protein kinase component of one regulatory system can phosphorylate the regulatory response protein of a second regulatory system. This suggests that the regulatory proteins might form a network of regulation.

The introduction of an additional set of regulatory proteins, not normally present within the cell, may interfere with the normal regulation of one or more cellular processes. The RprX and RprY proteins of this invention seem to interfere with the ability of the normal regulatory proteins to appropriately regulate their target by either altering the levels of phosphorylated versus non-phosphorylated regulatory proteins or by supplanting regulation by the normal regulating proteins and directly controlling expression of the target. The overall effect is manifested as a slow growth/small colony phenotype.

Because expression of RprX and/or RprY has a profound effect on the level of OmpF, and these two proteins are of the same regulatory protein family as EnvZ and OmpR, the normal regulators of OmpF expression, it is of interest to determine if RprX and/or RprY are "regulating" OmpF expression at the same level as EnvZ and OmpR. Normally, OmpF levels are controlled by regulating transcription of Using an ompF-lacZ operon fusion, it is determined that expression of wild-type RprX and RprY results in an 8–10 fold or greater decrease in the level of beta-galactosidase activity, while only a slight decrease in beta-galactosidase activity is observed when LacZ transcription and translation is directed by the lacZ promoter. This strongly indicates that RprX and RprY are affecting the level of transcription initiating from the ompF promoter and that the decrease in beta-galactosidase activity is not the result of decreased translation or stability of LacZ in the rprX and rprY expressing cells.

The ability of RprX and RprY to influence OmpF and OmpC protein levels at the level of transcription suggests that they elicit regulation in E. coli. This, in conjunction with the protein sequence homology data, suggests that the two proteins are regulatory proteins and would perform a regulatory function in B. fragilis, such as regulation of expression of B. fragilis outer membrane proteins or another cellular system.

Bibliography

1. Stock, J. B. et al., *Microbiol. Reviews*, 53, 450–490 (1989).
2. Stock, J. B., et al., *Nature*, 344, 395–400 (1990).
3. Comeau, D. E., et al., *J. Bacteriol.*, 164, 578–584 (1985).
4. Makino, K., et al., *J. Mol. Biol.*, 190, 37–44 (1986).
5. Makino, K., et al., *J. Mol Biol.*, 192, 549–556 (1986).
6. Stock, A., et al., *Pro. Natl. Acad. Sci. USA*, 85, 1403–1407 (1988).
7. Jin, S., et al., *J. Bacteriol.*, 172, 4945–4950 (1990).
8. Weiss, V. and Magasanik, B., *Proc. Natl. Acad. Sci. USA*, 85, 8919–8923 (1988).
9. Weber, R. F., and Silverman, P. M., *J. Mol. Biol.*, 203, 467–478 (1988).
10. Leroux, B., et al., *EMBO J.*, 6, 849–856 (1987).
11. Nixon, B. T., et al., *Proc. Natl. Acad. Sci. USA*, 83, 7850–7854 (1986).
12. Melchers, L. S., et al., *Nucleic Acids Research*, 14, 993–994 (1986).

13. Trach, K., et al., *J. Bacteriol.*, 170, 4194–4208 (1988).
14. Stock A., et al., *Proc. Natl. Acad. Sci. USA*, 82, 7989–7993 (1985).
15. Rasmussen, B. A., Gluzman, Y. and Tally, F. P., *Antimicrob. Agents. Chemother.*, 34, 1590–1592 (1990).
16. Rasmussen, B. A., Gluzman, Y. and Tally, F. P., *Molecular Microbiol.*, 5, 1211–1219 (1991).
17. Miller, J. H., Experiments in molecular genetics, page 433, Cold Spring Harbor Laboratory Press, Cold Spring Harbor, N.Y. (1972).
18. Sambrook, J., et al., *Molecular Cloning: A Laboratory Manual*, 2nd ed., Cold Spring Harbor Laboratory Press, Cold Spring Harbor, N.Y. (1989).
19. Sanger, F., et al., *Proc. Natl. Acad. Sci. USA*, 74, 5463–5467 (1977).
20. Vieira, J., and Messing, J., *Methods Enzymol.*, 153, 3–34 (1987).
21. Gold, L., and Stormo, G., "Translation initiation," pp. 1302–1307 in Neidhardt, F., et al., eds., *Escherichia coli and Salmonella typhimurium*, American Society for Microbiology, Washington, D.C. (1987).
22. Weisberg, G. W., et al., *J. Bacteriol.*, 164, 230–236 (1985).
23. Yager, T. D. and vonHippel, P. H., "Transcription and termination in *Escherichia coli*", pp. 1241–1275 in Neidhardt, F. C., et al., eds., *Escherichia coli and Salmonella typhimurium*, American Society for Microbiology, Washington, D.C. (1987).
24. Kyte, J., and Doolittle, R. F., *J. Mol. Biol.*, 157, 105–132 (1982).
25. Bankaitis, V. A., et al., *Cell*, 37, 243–252 (1984).
26. Hall, M. N., and Silhavy, T. J., *Mol. Biol.*, 146, 23–43 (1981).
27. Bachmann, B. J., "Derivations and genotypes of some mutant derivatives of *Escherichia coli* K-12", pp. 1190–1219 in Neidhardt, F. C., et al., eds., *Escherichia coli and Salmonella typhimurium*, American Society for Microbiology, Washington, D.C. (1987).
28. Salyers, A. A., et al., *Molecular Microbiol.*, 4, 151–156 (1990).
29. Cohen, S. P., et al., *Antimicrob. Agents Chemother.*, 33, 1318–1325 (1989).
30. Pugsley, A. P., and Schnaitman, C. A., *J. Bacteriol.*, 133, 1181–1189 (1978).
31. Igo, M. M., et al., *Genes Dev.*, 3, 1725–1734 (1989).
32. Ninfa, A. J., et al., *Proc. Natl. Acad. Sol. USA*, 85, 5492–5496 (1988).

What is claimed is:

1. A purified isolated DNA fragment of *Bacteroides fragilis* (*B. fragilis*) comprising a sequence for an operon encoding for RprX and RprY proteins.

2. The purified isolated DNA fragment of claim 1, wherein the fragment comprises a sequence which hybridizes under high stringency conditions with a sequence for an operon encoding for RprX and RprY proteins.

3. The purified isolated DNA fragment of claim 2, wherein the fragment comprises a sequence which hybridizes under high stringency conditions with the nucleic acid sequence of SEQ ID NO. 1.

4. A plasmid containing the purified isolated DNA fragment of *B. fragilis* comprising the sequence of claim 1.

5. The plasmid of claim 4 wherein the plasmid contains a purified isolated DNA fragment of *B. fragilis* comprising a sequence which hybridizes under high stringency conditions with a sequence for an operon encoding for RprX and RprY proteins.

6. The plasmid of claim 5 wherein the plasmid is that designated pCLL2230.

7. A host cell transformed with the plasmid of claim 4.

8. The host cell of claim 7 wherein the host cell is *Escherichia coli* DH5α.

9. The host cell of claim 8 wherein the plasmid is that designated pCLL2230 (ATCC 69246).

10. A method of producing RprX protein and RprY protein which comprises transforming a host cell with the plasmid of claim 4 and culturing the cell under conditions which permit expression of the proteins by the host cell.

11. A purified isolated DNA fragment of *B. fragilis* comprising a sequence encoding for RprX protein.

12. The purified isolated DNA fragment of claim 4, wherein the fragment comprises a sequence which hybridizes under high stringency conditions with a sequence encoding for RprX protein.

13. The purified isolated DNA fragment of claim 12, wherein the fragment comprises a sequence which hybridizes under high stringency conditions with the nucleotides numbered 266 to 1822 of SEQ ID NO. 1.

14. The purified isolated DNA fragment of claim 12, wherein the fragment comprises a sequence encoding for RprX protein whose amino acid sequence is depicted in SEQ ID NO. 2.

15. A purified isolated DNA fragment of *B. fragilis* comprising a sequence encoding for RprY protein.

16. The purified isolated DNA fragment of claim 15, wherein the fragment comprises a sequence which hybridizes under high stringency conditions with a sequence encoding for RprY protein.

17. The purified isolated DNA fragment of claim 16, wherein the fragment comprises a sequence which hybridizes under high stringency conditions with the nucleotides numbered 1818 to 2525 of SEQ ID NO. 1.

18. The purified isolated DNA fragment of claim 16, wherein the fragment comprises a sequence encoding for RprY protein whose amino acid sequence is depicted in residues numbered 1 to 236 of SEQ ID NO. 3.

19. The purified isolated DNA fragment of claim 16, wherein the fragment comprises a sequence which hybridizes under high stringency conditions with the nucleotides numbered 1827 to 2525 of SEQ ID NO. 1.

20. The purified isolated DNA fragment of claim 16, wherein the fragment comprises a sequence encoding for RprY protein whose amino acid sequence is depicted in residues numbered 4 to 236 of SEQ ID NO. 3.

* * * * *

UNITED STATES PATENT AND TRADEMARK OFFICE
CERTIFICATE OF CORRECTION

PATENT NO. : 5,679,540
DATED : October 21, 1997
INVENTOR(S) : Beth Ann Rasmussen It is certified that error appears in the above-indentified patent and that said Letters Patent is hereby corrected as shown below:

Col. 12, line 27: after "transcription of", add -ompF.--.

Col. 43, line 9: in Claim 12, change "of claim 4," to -of claim 11,--.

Signed and Sealed this

Fifth Day of October, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
      ( A ) LENGTH: 2651 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
GGTTGTAGCT    GCCGTTACAT    GCCATTGACA    GTTCGTCGGT    CGCCTCTTGA    AACCTGCTTA      60

CTCATTAACA    ATGATTAAAG    AAAGTAGATT    TTCTGAAGAG    AAATCTTTAA    TTTTTTATTA     120

AATTTGCAAA    CCAAAGGCAT    ATACGTTTTG    TTATAGTGGT    CAGAATACGA    CCTAAAAAAC     180

GTCTTTCGGT    TAATTATAGA    GAACATCCTG    TTAAAACAGG    TTAAGCTGTT    AGGAGTGTTA     240

ATTAGGGAGT    GTTAATTTTG    TTGCTATGAA    AAAGTCAACA    ATCTGGATAT    TAGGCATTAT     300

TATGGGTCTT    TCCTTTCTGA    GTTGGCTCTA    TTTACAAGTG    AGCTACATCG    AAGAAATGGT     360

GAGGATGCGT    AAAGAACAAT    TTAATACATC    CGTGCGAAAT    GCTTTGTTTC    AGGTTTCAAA     420

GGATGTGGAG    TATGATGAAA    CGCAACGTTG    GCTGTTAGAA    GACATTACTG    AAGCGGAACG     480

TAGAGCACTG    GCTCAGTCTT    CTTCTACTAC    CGAACAGAAA    AATGGTTTGA    TTCAGCAATC     540

GGAGCGTTAT    AGGTTCAAGT    CACCGGACGG    AACCCTGTAT    TCGGAGTTTG    AACTAAAGAT     600

GATTACCACC    GAGCCGTCGA    AGGTGCCCAA    AGCCATGATT    TCGGAGAGAC    ATGGCCGGAA     660

TACCATTCCG    CAGACATCGC    GAAGCTTGAC    CGACGCTATT    AAAAATAGGT    ATATGTATCA     720

GCGTTTCCTG    TCTGACGATG    TAGCTTTGCG    GATGATTTAC    AAAGCAAGCG    ATAAGTCGAT     780
```

-continued

| | | | | | |
|---|---|---|---|---|---|
| TGGCGAACGG | GTGAACTTTA | AGAAGCTGGA | TAATTATCTG | AAGTCTAACT | TTATTAATAA | 840 |
| TGGTATAGAG | CTGCTATATC | ATTTTTCGGT | AATCGATAAA | GATGGACGTG | AGGTATATCG | 900 |
| CTGTTCGGAT | TACGAAGAGG | GAGGAAGTGA | GGATTCTTAT | ACCCAACCTC | TGTTCCAAAA | 960 |
| TGATCCGCCT | GCGAAGATGA | GTATTGTGAA | GGTGCACTTT | CCGGGAAACA | AAGATTATAT | 1020 |
| CTTCGACTCG | GTTAGTTTTA | TGATCCCTTC | GATGATATTC | ACTTTCGTAC | TGTTGATTAC | 1080 |
| ATTCATCTTC | ACTATCTACA | TCGTCTTCCG | CCAGAAGAAG | CTGACAGAAA | TGAAGAATGA | 1140 |
| CTTTATCAAC | AATATGACAC | ACGAGTTCAA | GACACCGATA | TCTACCATCT | CGCTTGCCGC | 1200 |
| GCAGATGCTG | AAAGATCCCG | CATTCGGGAA | ATCACCGCAG | ATGTTCCAGC | ATATATCGGG | 1260 |
| AGTCATTAAT | GATGAAACGA | AGCGGTTGAG | ATTCCAGGTG | GAGAAAGTTC | TTCAGATGTC | 1320 |
| TATGTTCGAC | AGACAGAAAG | CAACACTGAA | GATGAAAGAA | CTCGATGCCA | ATGAGTTGAT | 1380 |
| TTCCGGGGTT | ATCAATACGT | TCGCTCTGAA | GGTGGAACGC | TATAATGGTA | AGATTACATC | 1440 |
| GAACCTTGAG | GCTACCAATC | CTGTTATATT | TGCGGACGAA | ATGCATATGA | CCAATGTGAT | 1500 |
| ATTCAACCTG | ATGGATAACG | CGGTGAAATA | CAAGAAGCCC | GAAGAAGACC | TGGTGCTCGA | 1560 |
| CGTGAGAACC | TGGAACGAAC | CCGGTAAACT | GATGATTTCG | ATACAGGACA | ACGGTATTGG | 1620 |
| TATTAAAAAA | GAAAACCTGA | AGAAGGTGTT | TGATAAGTTC | TATCGCTGTC | ATACAGGTAA | 1680 |
| TCTGCACGAT | GTAAAAGGTT | TCGGTCTGGG | ACTGGCTTAT | GTGAAAAGA | TTATTCAGGA | 1740 |
| TCATAAGGGA | ACCATCCGGG | CGGAGAGTGA | ACTGATTGTA | GGAACTAAAT | TTATTATTGC | 1800 |
| ATTACCTTTA | TTAAAAAATG | ATTGATATGG | ACGAGAAACT | GCGTATTTTA | TTATGCGAGG | 1860 |
| ATGATGAAAA | TCTTGGCATG | CTTTTAAGAG | AATATTTACA | GGCGAAAGGT | TACTCTGCTG | 1920 |
| AGTTGTATCC | TGATGGAGAA | GCCGGATTTA | AGGCTTTCCT | GAAGAATAAA | TATGACTTGT | 1980 |
| GCGTGTTCGA | CGTGATGATG | CCTAAGAAAG | ATGGTTTCAC | GCTGGCACAG | GAGGTTCGTG | 2040 |
| CGGCCAACGC | TGAAATTCCG | ATTATCTTCC | TGACTGCAAA | GACACTCAAG | GAGGATATTC | 2100 |
| TGGAAGGATT | TAAGATTGGT | GCGGATGATT | ACATCACCAA | ACCTTTCAGT | ATGGAAGAAC | 2160 |
| TTACTTTCAG | AATTGAAGCG | ATCCTGAGAC | GTGTTCGTGG | AAAGAAGAAC | AAAGAAAGCA | 2220 |
| ATATCTATAA | GATCGGTAAG | TTTACGTTTG | ATACACAAAA | GCAGATTCTG | GCTATCGGTG | 2280 |
| ACAAACAAAC | TAAGCTGACT | ACCAAGGAAT | CGGAATTGCT | GGGATTGCTG | TGTGCACATG | 2340 |
| CCAACGAGAT | TTTGCAGCGT | GACTTTGCTT | TGAAGACTAT | CTGGATTGAT | GATAACTATT | 2400 |
| TCAATGCCCG | TAGTATGGAC | GTATATATCA | CCAAACTGCG | TAAGCACCTG | AAGGATGATG | 2460 |
| ATTCGATTGA | GATTATCAAC | ATCCACGGAA | AAGGTTACAA | GTTGATTACC | CCCGAACCGG | 2520 |
| AATCATAATG | GAGAGGGGGA | TATACAGAAA | TAAAAAGCC | GGAAAACATT | CGTTTTCCGG | 2580 |
| CTTTTTTATT | TCTGTTGAAA | ATATTAATCC | GCAATTCTTT | TATTGATCGC | AATGTAAGAA | 2640 |
| ATGAGTCCGA | G | | | | | 2651 |

( 2 ) INFORMATION FOR SEQ ID NO:2:

( i ) SEQUENCE CHARACTERISTICS:
        ( A ) LENGTH: 519 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Met Lys Lys Ser Thr Ile Trp Ile Leu Gly Ile Ile Met Gly Leu Ser
1               5                   10                  15
Phe Leu Ser Leu Leu Tyr Leu Gln Val Ser Tyr Ile Glu Glu Met Val
            20                  25                  30
Lys Met Arg Lys Glu Gln Phe Asn Thr Ser Val Arg Asn Ala Leu Phe
            35                  40                  45
Gln Val Ser Lys Asp Val Glu Tyr Asp Glu Thr Gln Arg Trp Leu Leu
        50                  55                  60
Glu Asp Ile Thr Glu Ala Glu Arg Arg Ala Leu Ala Gln Ser Ser Ser
65                  70                  75                  80
Thr Thr Glu Gln Lys Asn Gly Leu Ile Gln Gln Ser Glu Arg Tyr Arg
                85                  90                  95
Phe Lys Ser Pro Asp Gly Thr Leu Tyr Ser Glu Phe Glu Leu Lys Met
            100                 105                 110
Ile Thr Thr Glu Pro Ser Lys Val Pro Lys Ala Met Ile Ser Glu Arg
        115                 120                 125
His Gly Arg Asn Thr Ile Pro Gln Thr Ser Arg Ser Leu Thr Asp Ala
    130                 135                 140
Ile Lys Asn Arg Tyr Met Tyr Gln Arg Phe Leu Leu Asp Asp Val Ala
145                 150                 155                 160
Leu Arg Met Ile Tyr Lys Ala Ser Asp Lys Ser Ile Gly Glu Arg Val
                165                 170                 175
Asn Phe Lys Lys Leu Asp Asn Tyr Leu Lys Ser Asn Phe Ile Asn Asn
            180                 185                 190
Gly Ile Glu Leu Leu Tyr His Phe Ser Val Ile Asp Lys Asp Gly Arg
        195                 200                 205
Glu Val Tyr Arg Cys Ser Asp Tyr Glu Glu Gly Gly Ser Glu Asp Ser
    210                 215                 220
Tyr Thr Gln Pro Leu Phe Gln Asn Asp Pro Pro Ala Lys Met Ser Ile
225                 230                 235                 240
Val Lys Val His Phe Pro Gly Lys Lys Asp Tyr Ile Phe Asp Ser Val
                245                 250                 255
Ser Phe Met Ile Pro Ser Met Ile Phe Thr Phe Val Leu Leu Ile Thr
            260                 265                 270
Phe Ile Phe Thr Ile Tyr Ile Val Phe Arg Gln Lys Lys Leu Thr Glu
        275                 280                 285
Met Lys Asn Asp Phe Ile Asn Asn Met Thr His Glu Phe Lys Thr Pro
    290                 295                 300
Ile Ser Thr Ile Ser Leu Ala Ala Gln Met Leu Lys Asp Pro Ala Val
305                 310                 315                 320
Gly Lys Ser Pro Gln Met Phe Gln His Ile Ser Gly Val Ile Asn Asp
                325                 330                 335
Glu Thr Lys Arg Leu Arg Phe Gln Val Glu Lys Val Leu Gln Met Ser
            340                 345                 350
Met Phe Asp Arg Gln Lys Ala Thr Leu Lys Met Lys Glu Leu Asp Ala
        355                 360                 365
Asn Glu Leu Ile Ser Gly Val Ile Asn Thr Phe Ala Leu Lys Val Glu
    370                 375                 380
Arg Tyr Asn Gly Lys Ile Thr Ser Asn Leu Glu Ala Thr Asn Pro Val
385                 390                 395                 400
Ile Phe Ala Asp Glu Met His Ile Thr Asn Val Ile Phe Asn Leu Met
                405                 410                 415
Asp Asn Ala Val Lys Tyr Lys Lys Pro Glu Glu Asp Leu Val Leu Asp
```

```
                        420                        425                        430
    Val  Tyr  Thr  Trp  Asn  Glu  Pro  Gly  Lys  Leu  Met  Ile  Ser  Ile  Gln  Asp
              435                      440                     445

Asn  Gly  Ile  Gly  Ile  Lys  Lys  Glu  Asn  Leu  Lys  Lys  Val  Phe  Asp  Lys
         450                      455                     460

Phe  Tyr  Arg  Val  His  Thr  Gly  Asn  Leu  His  Asp  Val  Lys  Gly  Phe  Gly
    465                      470                     475                          480

Leu  Gly  Leu  Ala  Tyr  Val  Lys  Lys  Ile  Ile  Gln  Asp  His  Lys  Gly  Thr
                        485                      490                          495

Ile  Arg  Ala  Glu  Ser  Glu  Leu  Asn  Val  Gly  Thr  Lys  Phe  Ile  Ile  Ala
                   500                      505                     510

Leu  Pro  Leu  Leu  Lys  Asn  Asp
                   515
```

( 2 ) INFORMATION FOR SEQ ID NO:3:

( i ) SEQUENCE CHARACTERISTICS:
        ( A ) LENGTH: 236 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

```
    Met  Ile  Asp  Met  Asp  Glu  Lys  Leu  Arg  Ile  Leu  Leu  Cys  Glu  Asp  Asp
    1              5                        10                      15

Glu  Asn  Leu  Gly  Met  Leu  Leu  Arg  Glu  Tyr  Leu  Gln  Ala  Lys  Gly  Tyr
                   20                      25                      30

Ser  Ala  Glu  Leu  Tyr  Pro  Asp  Gly  Glu  Ala  Gly  Phe  Lys  Ala  Phe  Leu
                   35                      40                      45

Lys  Asn  Lys  Tyr  Asp  Leu  Cys  Val  Phe  Asp  Val  Met  Met  Pro  Lys  Lys
         50                      55                      60

Asp  Gly  Phe  Thr  Leu  Ala  Gln  Glu  Val  Arg  Ala  Ala  Asn  Ala  Glu  Ile
    65                      70                      75                          80

Pro  Ile  Ile  Phe  Leu  Thr  Ala  Lys  Thr  Leu  Lys  Glu  Asp  Ile  Leu  Glu
                        85                      90                      95

Gly  Phe  Lys  Ile  Gly  Ala  Asp  Asp  Tyr  Ile  Thr  Lys  Pro  Phe  Ser  Met
                   100                     105                     110

Glu  Glu  Leu  Thr  Phe  Tyr  Ile  Glu  Ala  Ile  Leu  Arg  Arg  Val  Arg  Gly
                   115                     120                     125

Lys  Lys  Asn  Lys  Glu  Ser  Asn  Ile  Tyr  Lys  Ile  Gly  Lys  Phe  Thr  Phe
         130                     135                     140

Asp  Thr  Gln  Lys  Gln  Ile  Leu  Ala  Ile  Gly  Asp  Lys  Gln  Thr  Lys  Leu
    145                     150                     155                         160

Thr  Thr  Lys  Glu  Ser  Glu  Leu  Leu  Gly  Leu  Leu  Cys  Ala  His  Ala  Asn
                        165                     170                     175

Glu  Ile  Leu  Gln  Arg  Asp  Phe  Ala  Leu  Lys  Thr  Ile  Trp  Ile  Asp  Asp
                   180                     185                     190

Asn  Tyr  Phe  Asn  Ala  Arg  Ser  Met  Asp  Val  Tyr  Ile  Thr  Lys  Leu  Arg
                   195                     200                     205

Lys  His  Leu  Lys  Asp  Asp  Asp  Ser  Ile  Glu  Ile  Ile  Asn  Ile  His  Gly
         210                     215                     220

Lys  Gly  Tyr  Lys  Leu  Ile  Thr  Pro  Glu  Pro  Glu  Ser
```

(2) INFORMATION FOR SEQ ID NO:4:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

Asp Ile Ser His Glu Leu Arg Thr Pro Leu Thr
   1               5                   10

(2) INFORMATION FOR SEQ ID NO:5:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

Pro Asn Ala Leu Glu Ser Ala Leu Glu Asn Ile Val Arg Asn Ala
   1               5                   10                  15

(2) INFORMATION FOR SEQ ID NO:6:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

Val Asp Asp Asp Gly Pro Gly Val Ser Pro
   1               5                   10

(2) INFORMATION FOR SEQ ID NO:7:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:7:

Gly Gly Thr Gly Pro Gly Pro Ala Ile Val ( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

Asn Val Ser His Glu Leu Arg Thr Pro Leu Thr
    1             5                  10

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

Glu Asp Gln Leu Arg Ser Ala Ile Ser Asn Leu Val Tyr Asn Ala
    1             5                  10               15

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:10:

Val Glu Asp Asn Gly Pro Gly Ile Ala Pro
    1             5                  10

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:11:

Gly Gly Ser Gly Leu Gly Leu Ser Ile Ala ( 2 ) INFORMATION FOR SEQ ID NO:12:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:12:

```
Arg Ala Ala His Ser Ile Lys Gly Gly Ala Gly
1               5                   10
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:13:

```
Pro Glu Lys Thr Leu Glu Ala Gly Lys Asn Val Val Gly Asn Leu
1               5                   10                  15
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:14:

```
Val Thr Asp Asp Gly Ala Gly Leu Asn Thr
1               5                   10
```

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:15:

```
Ser Gly Arg Gly Val Gly Met Asp Val Val
```

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:16:

```
Gly Ile Ala His Glu Phe Asn Asn Ile Leu Gly
1               5                   10
```

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:17:

```
Pro Leu Glu Leu Gln Gln Val Leu Ile Asn Ile Cys Lys Asn Ala
1               5                   10                  15
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:18:

```
Ile Ser Asp Asn Gly Gly Gly Ile Pro Glu
1               5                   10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:19:

```
Gly Gly Thr Gly Leu Gly Leu Ala Ser Val
```

( 2 ) INFORMATION FOR SEQ ID NO:20:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:20:

```
Met Leu Ala His Glu Ile Lys Asn Pro Leu Ser
1               5                   10
```

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:21:

```
Gln Asp Gln Leu Ile Gln Val Phe Leu Asn Leu Val Lys Asn Ala
1               5                   10                  15
```

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:22:

```
Val Lys Asp Asn Gly Ser Gly Val Pro Glu
1               5                   10
```

( 2 ) INFORMATION FOR SEQ ID NO:23:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:23:

```
Thr Gly Ser Gly Leu Gly Leu Ala Leu Val
```

( 2 ) INFORMATION FOR SEQ ID NO:24:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:24:

```
Met Gln Glu Asn Tyr Lys Asn Leu Val Val Asp Asp Asp Met Arg Leu
 1               5                  10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
            35                  40                  45

Phe His Leu Met Val Leu Asp Leu Met Leu Pro Gly Glu Asp Gly Leu
        50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
                100                 105                 110

Leu Ala Arg Ile Arg Pro Val Leu Arg Arg Gln Ala Asn
            115                 120             125
```

( 2 ) INFORMATION FOR SEQ ID NO:25:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:25:

```
Glu Pro Leu Lys His Val Leu Leu Val Asp Asp Val Ala Met Arg
 1               5                  10                  15

His Leu Ile Ile Glu Tyr Leu Thr Ile His Ala Phe Lys Val Thr Ala
            20                  25                  30

Val Ala Asp Ser Thr Gln Phe Thr Arg Val Leu Ser Ser Ala Thr Val
            35                  40                  45

Asp Val Val Val Val Asp Leu Asn Leu Gly Arg Glu Asp Gly Leu Glu
        50                  55                  60

Ile Val Arg Asn Leu Ala Ala Lys Ser Asp Ile Pro Ile Ile Ile Ile
65                  70                  75                  80

Ser Gly Asp Arg Leu Glu Glu Thr Asp Lys Val Val Ala Leu Glu Leu
                85                  90                  95

Gly Ala Ser Asp Phe Ile Ala Lys Pro Phe Ser Ile Arg Glu Phe Leu
                100                 105                 110
```

Ala Arg Ile Arg Val Ala Leu Arg Val Arg Pro Asn
            115                 120

( 2 ) INFORMATION FOR SEQ ID NO:26:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:26:

Met Pro Ala Gly Ser Ile Leu Val Ala Asp Asp Thr Ala Ile Arg
1               5                   10                  15

Thr Val Leu Asn Gln Ala Leu Ser Arg Ala Gly Tyr Glu Val Arg Leu
            20                  25                  30

Thr Gly Asn Ala Ala Thr Leu Trp Arg Trp Val Ser Gln Gly Glu Gly
            35                  40                  45

Asp Leu Val Ile Thr Asp Val Val Met Pro Asp Glu Asn Ala Phe Asp
    50                  55                  60

Leu Leu Pro Arg Ile Lys Lys Met Arg Pro Asn Leu Pro Val Ile Val
65                  70                  75                  80

Met Ser Ala Gln Asn Thr Phe Met Thr Ala Ile Arg Pro Ser Glu Arg
                85                  90                  95

Gly Ala Tyr Glu Tyr Leu Pro Lys Pro Phe Asp Leu Lys Glu Leu Ile
            100                 105                 110

Thr Ile Val Gly Arg Ala Leu Ala Glu Pro Lys Glu
            115                 120

( 2 ) INFORMATION FOR SEQ ID NO:27:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:27:

Met Ala Arg Arg Ile Leu Val Val Glu Asp Glu Ala Pro Ile Arg Glu
1               5                   10                  15

Met Val Cys Phe Val Leu Glu Gln Asn Gly Phe Gln Pro Val Glu Ala
            20                  25                  30

Glu Asp Tyr Asp Ser Ala Val Asn Gln Leu Asn Glu Pro Trp Pro Asp
            35                  40                  45

Leu Ile Leu Leu Asp Trp Met Leu Pro Gly Gly Ser Gly Ile Gln Phe
    50                  55                  60

Ile Lys His Leu Lys Arg Glu Ser Met Thr Arg Asp Ile Pro Val Val
65                  70                  75                  80

Met Leu Thr Ala Arg Gly Glu Glu Glu Asp Arg Val Arg Gly Leu Glu
                85                  90                  95

```
Thr Gly Ala Asp Asp Tyr Ile Thr Lys Pro Phe Ser Pro Lys Glu Leu
            100                 105                 110

Val Ala Arg Ile Lys Ala Val Met Arg Arg Ile Ser Pro
            115                 120             125
```

( 2 ) INFORMATION FOR SEQ ID NO:28:

( i ) SEQUENCE CHARACTERISTICS:
    ( A ) LENGTH: 124 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:28:

```
Met Met Asn Glu Lys Ile Leu Ile Val Asp Asp Gln Tyr Gly Ile Arg
1               5                   10                  15

Ile Leu Leu Asn Glu Val Phe Asn Lys Glu Gly Tyr Gln Thr Phe Gln
            20                  25                  30

Ala Ala Asn Gly Leu Gln Ala Leu Asp Ile Val Thr Lys Glu Arg Pro
            35                  40                  45

Asp Leu Val Leu Leu Asp Met Lys Ile Pro Gly Met Asp Gly Ile Glu
            50                  55                  60

Ile Leu Lys Arg Met Lys Val Ile Asp Glu Asn Ile Arg Val Ile Ile
65                  70                  75                  80

Met Thr Ala Tyr Gly Glu Leu Asp Met Ile Gln Glu Ser Lys Glu Leu
                85                  90                  95

Gly Ala Leu Thr His Phe Ala Lys Pro Phe Asp Ile Asp Glu Ile Arg
            100                 105                 110

Asp Ala Val Lys Lys Tyr Leu Pro Leu Lys Ser Asn
            115                 120
```

( 2 ) INFORMATION FOR SEQ ID NO:29:

( i ) SEQUENCE CHARACTERISTICS:
    ( A ) LENGTH: 129 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:29:

```
Met Ala Asp Lys Glu Leu Lys Phe Leu Val Val Asp Asp Phe Ser Thr
1               5                   10                  15

Met Arg Arg Ile Val Arg Asn Leu Leu Lys Glu Leu Gly Phe Asn Asn
            20                  25                  30

Val Glu Glu Ala Glu Asp Gly Val Asp Ala Leu Asn Lys Leu Gln Ala
            35                  40                  45

Gly Gly Phe Gly Pro Ile Ile Ser Asp Trp Asn Met Pro Asn Met Asp
            50                  55                  60

Gly Leu Glu Leu Leu Lys Thr Ile Arg Ala Asp Ser Ala Met Ser Ala
65                  70                  75                  80

Leu Pro Val Leu Met Val Thr Ala Glu Ala Lys Lys Glu Asn Ile Ile
```

```
                          85                        90                            95
        Ala  Ala  Ala  Gln  Ala  Gly  Ala  Ser  Gly  Tyr  Val  Val  Lys  Pro  Phe  Thr
                          100                       105                           110

Ala  Ala  Thr  Leu  Glu  Glu  Lys  Leu  Asn  Lys  Ile  Phe  Glu  Lys  Leu  Gly
                          115                       120                           125

Met
```

( 2 ) INFORMATION FOR SEQ ID NO:30:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:30:

```
   Asn  Met  Thr  His  Glu  Phe  Lys  Thr  Pro  Ile  Ser
   1                   5                        10
```

( 2 ) INFORMATION FOR SEQ ID NO:31:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:31:

```
   Glu  Met  His  Ile  Thr  Asn  Val  Ile  Phe  Asn  Leu  Met  Asp  Asn  Ala
   1                   5                         10                       15
```

( 2 ) INFORMATION FOR SEQ ID NO:32:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:32:

```
   Ile  Gln  Asp  Asn  Gly  Ile  Gly  Ile  Lys  Tyr
   1                   5                        10
```

( 2 ) INFORMATION FOR SEQ ID NO:33:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: protein (i i i) HYPOTHETICAL: NO (i v) ANTI-SENSE: NO (x i) SEQUENCE DESCRIPTION: SEQ ID NO:33:

Lys Gly Phe Gly Leu Gly Leu Ala Tyr Val
1               5                   10

(2) INFORMATION FOR SEQ ID NO:34:

(i) SEQUENCE CHARACTERISTICS:
      (A) LENGTH: 32 amino acids
      (B) TYPE: amino acid
      (C) STRANDEDNESS: single
      (D) TOPOLOGY: linear (i i) MOLECULE TYPE: protein (i i i) HYPOTHETICAL: NO (i v) ANTI-SENSE: NO (x i) SEQUENCE DESCRIPTION: SEQ ID NO:34:

Met Ile Asp Met Asp Glu Lys Leu Arg Ile Leu Leu Cys Glu Asp Asp
1               5                   10                  15

Glu Asn Leu Gly Met Leu Leu Arg Glu Tyr Leu Gln Ala Lys Gly Tyr
            20                  25                  30

(2) INFORMATION FOR SEQ ID NO:35:

(i) SEQUENCE CHARACTERISTICS:
      (A) LENGTH: 34 amino acids
      (B) TYPE: amino acid
      (C) STRANDEDNESS: single
      (D) TOPOLOGY: linear (i i) MOLECULE TYPE: protein (i i i) HYPOTHETICAL: NO (i v) ANTI-SENSE: NO (x i) SEQUENCE DESCRIPTION: SEQ ID NO:35:

Ser Ala Glu Leu Tyr Pro Asp Gly Glu Ala Gly Phe Lys Ala Phe Leu
1               5                   10                  15

Lys Asn Lys Tyr Asp Leu Cys Val Phe Asp Val Met Met Pro Lys Lys
            20                  25                  30

Asp Gly (2) INFORMATION FOR SEQ ID NO:36:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: protein (i i i) HYPOTHETICAL: NO (i v) ANTI-SENSE: NO (x i) SEQUENCE DESCRIPTION: SEQ ID NO:36:

Phe Thr Leu Ala Gln Glu Val Arg Ala Ala Asn Ala
1               5                   10

(2) INFORMATION FOR SEQ ID NO:37:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:37:

```
Glu  Ile  Pro  Ile  Ile  Phe  Leu  Thr  Ala
 1                  5
```

( 2 ) INFORMATION FOR SEQ ID NO:38:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:38:

```
Lys  Thr  Leu  Lys  Glu  Asp  Ile  Leu  Glu  Gly  Phe  Lys  Ile  Gly  Ala  Asp
 1                  5                            10                       15
Asp  Tyr  Ile  Thr  Lys  Pro  Phe  Ser  Met  Glu  Glu  Leu  Thr  Phe  Arg  Ile
               20                       25                            30
Glu  Ala  Ile  Leu  Arg  Arg  Val  Arg  Gly
          35                    40
```

( 2 ) INFORMATION FOR SEQ ID NO:39:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:39:

```
Asp  Xaa  Gly  Xaa  Gly
 1                  5
```